(12) United States Patent
Han et al.

(10) Patent No.: US 8,871,509 B2
(45) Date of Patent: Oct. 28, 2014

(54) NANOPARTICLE-BASED GENE DELIVERY SYSTEMS

(75) Inventors: Min Su Han, Seoul (KR); Kangseok Lee, Seoul (KR); Dong-Eun Kim, Seoul (KR)

(73) Assignee: Chung-Ang University-Academy Corporation Foundation, Seoul (KR)

( * ) Notice: Subject to any disclaimer, the term of this patent is extended or adjusted under 35 U.S.C. 154(b) by 585 days.

(21) Appl. No.: 12/809,996

(22) PCT Filed: Mar. 18, 2010

(86) PCT No.: PCT/KR2010/001679
§ 371 (c)(1),
(2), (4) Date: Jun. 21, 2010

(87) PCT Pub. No.: WO2011/055888
PCT Pub. Date: May 12, 2011

(65) Prior Publication Data
US 2011/0229966 A1    Sep. 22, 2011

(30) Foreign Application Priority Data

Nov. 6, 2009  (KR) .................. 10-2009-0107234
Mar. 18, 2010 (KR) .................. 10-2010-0024120

(51) Int. Cl.
| | | |
|---|---|---|
| C12N 5/00 | (2006.01) | |
| C12N 5/02 | (2006.01) | |
| C07H 21/02 | (2006.01) | |
| C12N 15/11 | (2006.01) | |
| C12N 15/87 | (2006.01) | |
| C12N 15/113 | (2010.01) | |
| C12N 15/89 | (2006.01) | |
| A61K 47/48 | (2006.01) | |
| A61K 31/713 | (2006.01) | |
| A61K 31/7105 | (2006.01) | |

(52) U.S. Cl.
CPC ............ *C12N 15/113* (2013.01); *C12N 15/111* (2013.01); *C12N 15/87* (2013.01); *C12N 2320/32* (2013.01); *C12N 2310/127* (2013.01); *C12N 2310/14* (2013.01); *C12N 2310/11* (2013.01); *C12N 2310/351* (2013.01); *C12N 15/89* (2013.01); *C12N 2310/51* (2013.01); *A61K 47/48861* (2013.01); *C12N 2310/531* (2013.01); *A61K 31/713* (2013.01); *A61K 31/7105* (2013.01); *Y10S 977/773* (2013.01)
USPC .................. 435/375; 536/23.1; 977/773

(58) Field of Classification Search
None
See application file for complete search history.

(56) References Cited

U.S. PATENT DOCUMENTS 7,332,586 B2 *   2/2008  Franzen et al. ............... 530/402
2009/0148535 A1 * 6/2009  Bamdad ....................... 424/499

OTHER PUBLICATIONS

Kim, et al. (2010) "A functionalized gold nanoparticles-assisted universal carrier for antisense DNA", Chemical Communications, 46(23): 4151-53.*
Ryou, et al. (2010) "Delivery of shRNA using gold nanoparticle-DNA oligonucleotide conjugates as a universal carrier", Biochemical and Biophysical Research Communications, 398(3): 542-46.*
2005 NIH News, "New Genome Comparison Finds Chimps, Humans Very Similar at the DNA Level", National Institutes of Health, U.S. Department of Health and Human Services, by Geoff Spencer, obtained at http://www.genome.gov/pfv.cfm?pageID=15515096, no author, no volume.*
U.S. Department of Energy Genome Project, Human Genome News FAQ, Jul.-Sep. 1996, 8(1), obtained from http://www.ornl.gov/sci/techresources/Human_Genome/publicat/hgn/v8n1/16faq.shtml, no author, no volume, no number.*
Agbasi-Porter et al., "Transcription Inhibition Using Oligonucleotide-Modified Gold Nanoparticles," Bioconjug. Chem. 17:1178-1183, 2006.
Cheon et al., "Synergistically Integrated Nanoparticles as Multimodal Probes for Nanobiotechnology," Acc. Chem. Res. 41:1630-1640, 2008.
Daniel et al., "Gold Nanoparticles: Assembly, Supramolecular Chemistry, Quantum-Size-Related Properties, and Applications toward Biology, Catalysis, and Nanotechnology," Chem. Rev. 104:293-346, 2004.
Ghosh et al., "Efficient Gene Delivery Vectors by Tuning the Surface Charge Density of Amino Acid-Functionalized Gold Nanoparticles," Am. Chem. Soc. 2:2213-2218, 2008.
Green et al., "A Combinatorial Polymer Library Approach Yields Insight into Nonviral Gene Delivery," Acc. Chem. Res. 41:749-759, 2008.

(Continued)

*Primary Examiner* — Robert M Kelly
(74) *Attorney, Agent, or Firm* — Clark & Elbing LLP

(57) ABSTRACT

The present invention provides a gene delivery system containing nanoparticles. In more detail, the present invention provides a gene delivery system containing (a) a nanomaterial; (b) an oligonucleotide as an universal binding partner covalently linked to the surface of the nanomaterial; and (c) a cargo comprising (i) a complementary oligonucleotide containing a nucleotide sequence complementary to the universal binding partner as a binding counter-partner, and (ii) an inhibitory molecule having a nucleotide sequence complementary to a target gene of interest to be inhibited or an inducible molecule having a nucleotide sequence of a target gene of interest to be expressed. The present invention is a gene delivery system capable of feasibly deliver aptamer, siRNA, shRNA, miRNA, ribozyme, DNAzyme, PNA or gene as well as antisense oligonucleotide into the cells. In addition, the present invention is more efficient than the commercially available gene transfer reagent in respect to the degree of knockdown of target protein expression.

4 Claims, 31 Drawing Sheets

(56) References Cited

OTHER PUBLICATIONS

Guo et al., "Chemical Approaches to Triggerable Lipid Vesicles for Drug and Gene Delivery," Acc. Chem. Res. 36:335-341, 2003.

Kay et al., "Viral Vectors for Gene Therapy: The Art of Turning Infectious Agents into Vehicles of Therapeutics," Nat. Med. 7:33-40, 2001.

McCormick, "Cancer Gene Therapy: Fringe or Cutting Edge?" Nat. Rev. Cancer 1:130-141, 2001.

Mintzer et al., "Nonviral Vectors for Gene Delivery," Chem. Rev. 109:259-302, 2009.

Murphy et al., "Gold Nanoparticles in Biology: Beyond Toxicity to Cellular Imaging," Acc. Chem. Res. 41:1721-1730, 2008.

Opalinska et al., "Nucleic-Acid Therapeutics: Basic Principles and Recent Applications," Nat. Rev. Drug Discov. 1:503-514, 2002.

Prato et al., "Functionalized Carbon Nanotubes in Drug Design and Discovery," Acc. Chem. Res. 41:60-68, 2008.

Raper et al., "Fatal Systemic Inflammatory Response Syndrome in a Ornithine Transcarbamylase Deficient Patient Following Adenoviral Gene Transfer," Mol. Genet. Metab. 80:148-158, 2003.

Rosi et al., "Oligonulceotide-Modified Gold Nanoparticles for Intracellular Gene Regulation," Science 312:1027-1030, 2006.

Sandhu et al., "Gold Nanoparticle-Mediated Transfection of Mammalian Cells," Bioconjug. Chem. 13:3-6, 2002.

Slowing et al., "Mesoporous Silica Nanoparticles as Controlled Release Drug Delivery and Gene Transfection Carriers," Adv. Drug Deliv. Rev. 60:1278-1288, 2008.

Soppimath et al., "Biodegradable Polymeric Nanoparticles as Drug Delivery Devices," J. Control. Release 70:1-20, 2001.

Tekade et al., "Dendrimers in Oncology: An Expanding Horizon," Chem. Rev. 109:49-87, 2009.

Thomas et al., "Conjugation to Gold Nanoparticles Enhances Polyethylenimine's Transfer of Plasmid DNA into Mammalian Cells," Proc. Natl. Acad. Sci. U.S.A. 100:9138-9143, 2003.

Trewyn et al., "Synthesis and Functionalization of a Mesoporous Silica Nanoparticle Based on the Sol-Gel Process and Applications in Controlled Release," Acc. Chem. Res. 40:846-853, 2007.

Tsai et al., "A Biological Strategy for Fabrication of Au/EGFP Nanoparticle Conjugates Retaining Bioactivity," Nano Letters 4:1209-1212, 2004.

Verma et al., "Gene Therapy—Promises, Problems and Prospects," Nature 389:239-242, 1997.

\* cited by examiner

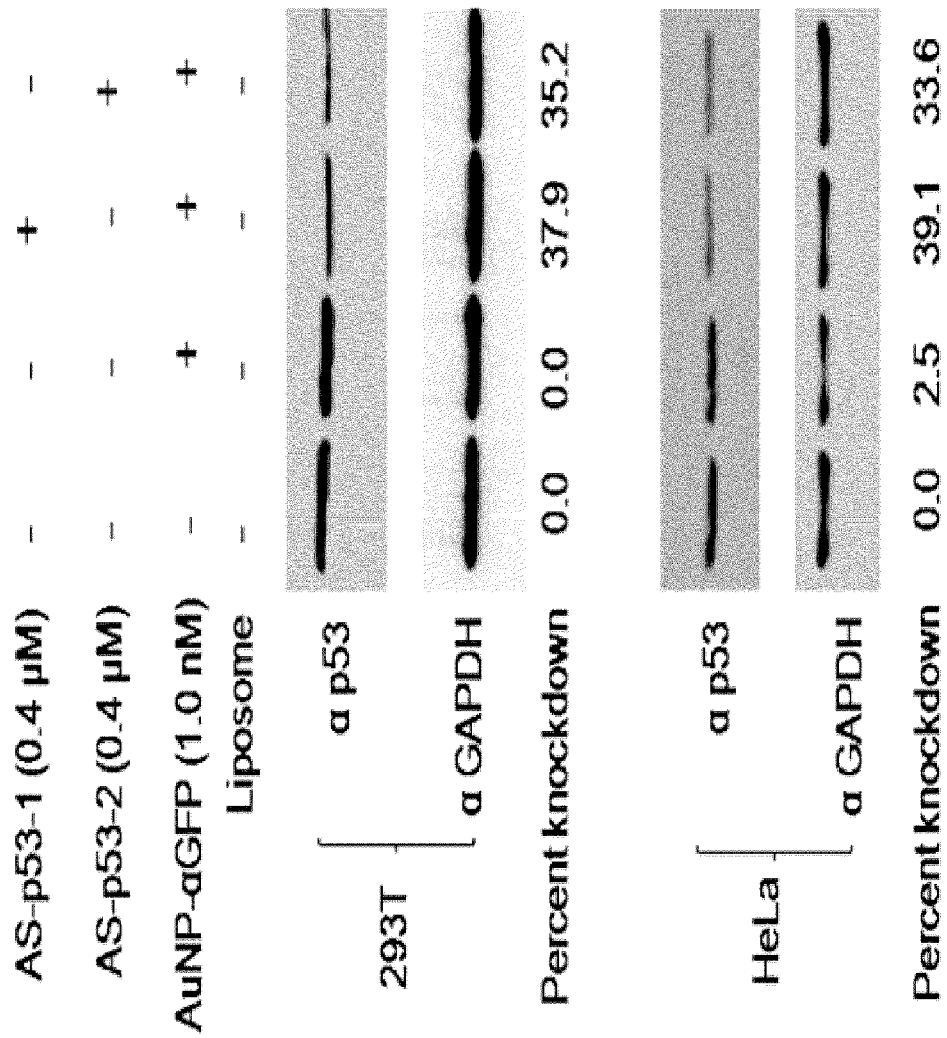

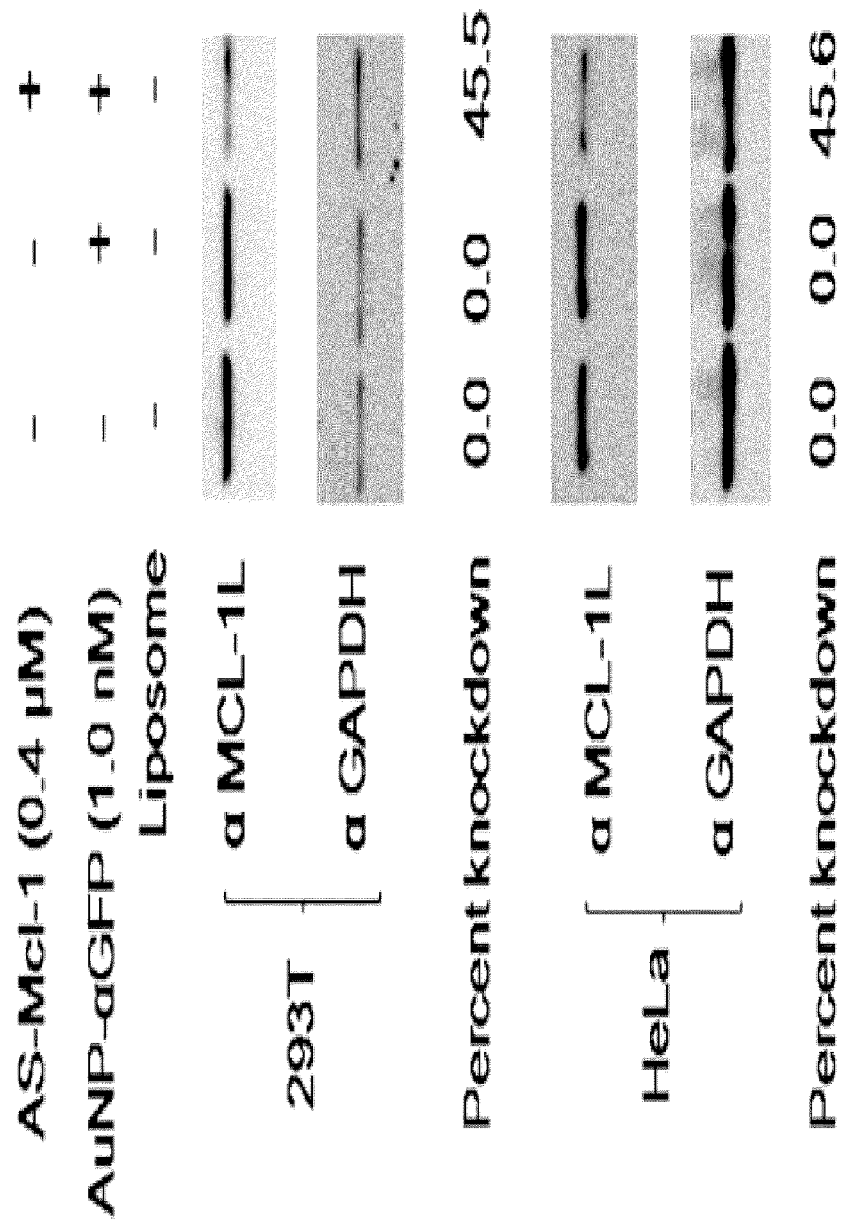

Fig. 7b

AuNP oligo 2 (RNA I): 3'-thiol-Alkyl-(A)10-GCGATCGTCTGGCTCTA-5'  SEQ ID NO:7

SEQ ID NO:24  Antisense-p53-1: 5'-CTCTAGCAGACCGGCAGAT CCCTGCTCCCCTGGCTCC-3' anti GNP oligo 2    complementary to p53

Fig. 8b

AuNP oligo 1 (anti-GFP): 3'-HS(CH₂)₆A₁₀-CTGCCGTCGCACGTCGAG-5'
SEQ ID NO:1

SEQ ID NO:27 anti p53 sh RNA: 5'-GGGACGGGACAGCUGCAGCUCGACUCCAGUGGUAAUCUACUGAAGA
                                  -GUAGAUUACCACUGGAGUCGU-3' p53 shRNA
SEQ ID NO:6

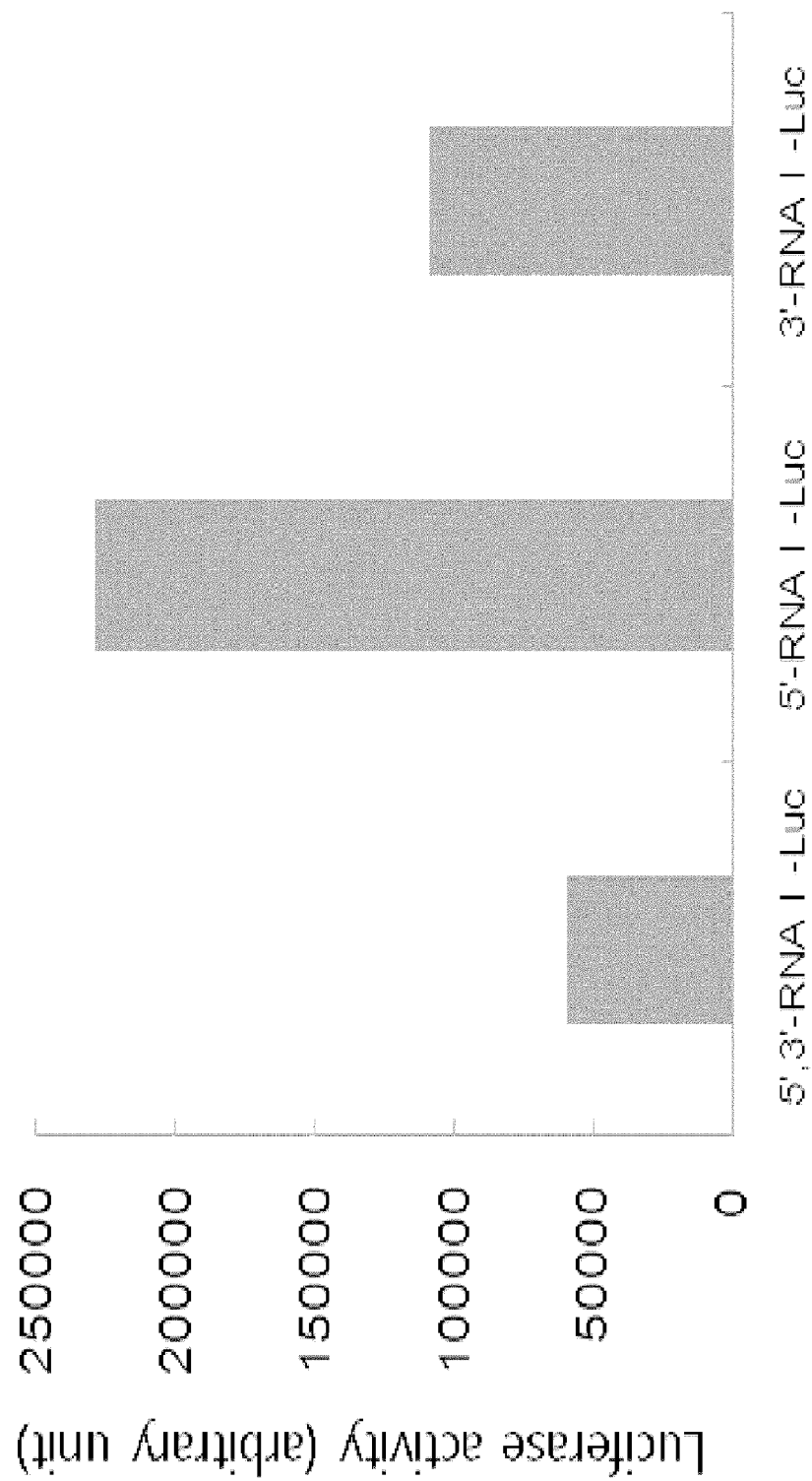

Fig. 9c

Luc-S1: 5'-GGATCTGCATCTCAATTAG SEQ ID NO:28
complementary to pGL3-Control (2450-2431)

RNAi-Luc-S1: 5'-CTCTAGCAGAGGCAGAT-C6 LINKER-GGCATCTGCATCTCAATTAG SEQ ID NO:29
complementary to AJNP-RNAi    complementary to pGL3-Control (2450-2431)

Luc-AS1: 5'-GACGGATCCGTGTGGAATG SEQ ID NO:30
complementary to pGL3-Control (42-61)

RNAi-Luc-AS1: 5'-CTCTAGCAGAGGCAGAT-C6 LINKER-GACGGATCCGTGTGGAATG SEQ ID NO:31
complementary to AJNP-RNAi    complementary to pGL3-Control (42-61)

Fig. 13a
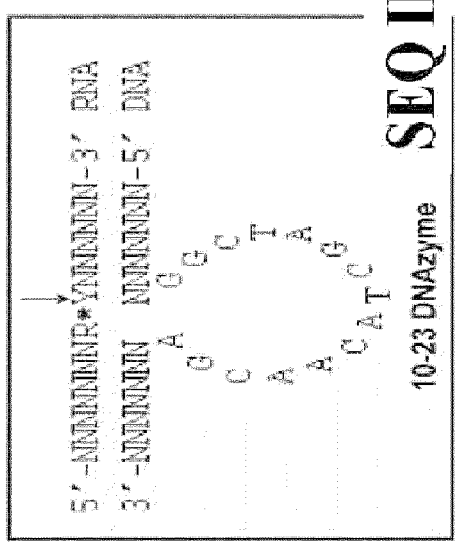
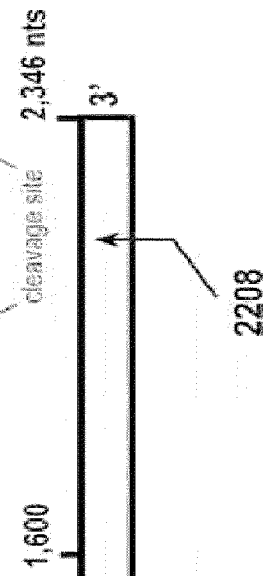
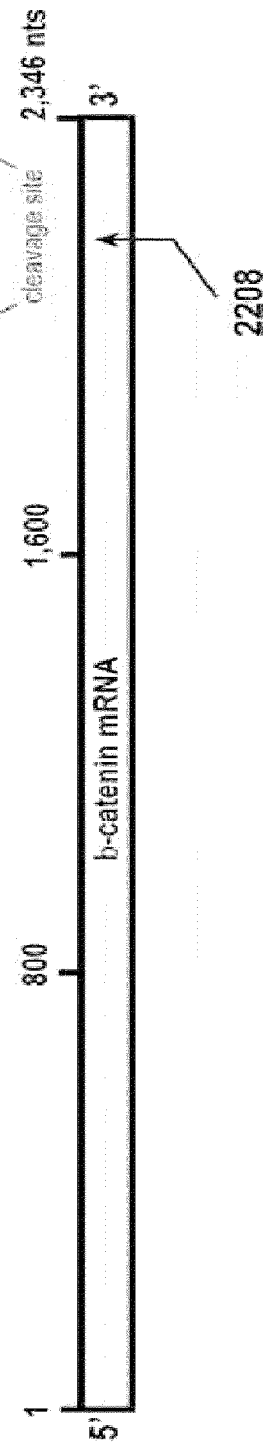

Tetra-thiol oligonucleotides : SEQ ID NO:25

Antisense : 3' (DTPA)₂ A-A-AAAAAAACTGCCGTCGGCAGTCG-A-G
5' CGTGCAGC-CATCTCATG  TCCATCATG 3'

SEQ ID NO:26    GFP antisense-Dz2208 DNAzyme

Fig. 14c
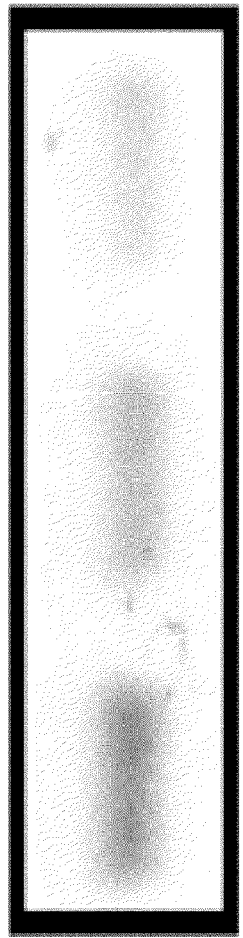 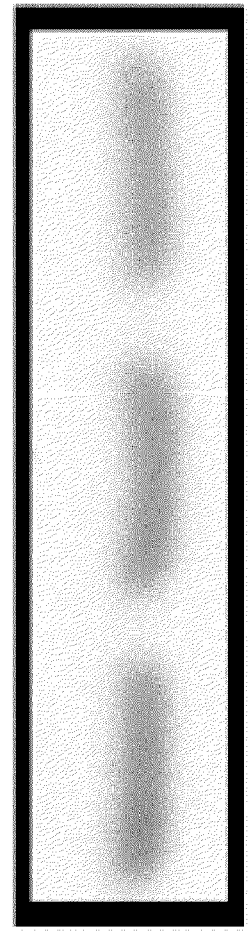

SEQUENCE LISTING

<160> NUMBER OF SEQ ID NOS: 35

<210> SEQ ID NO 1
<211> LENGTH: 18
<212> TYPE: DNA
<213> ORGANISM: Unknown
<220> FEATURE:
<223> OTHER INFORMATION: EGFP DNA oligonucleotide

<400> SEQUENCE: 1

-continued gagctgcacg ctgccgtc                                                 18

<210> SEQ ID NO 2
<211> LENGTH: 18
<212> TYPE: DNA
<213> ORGANISM: Artificial Sequence
<220> FEATURE:
<223> OTHER INFORMATION: anti-EGFP-oligonucleotide

<400> SEQUENCE: 2
ctcgacgtgc gacggcag                                                 18

<210> SEQ ID NO 3
<211> LENGTH: 20
<212> TYPE: DNA
<213> ORGANISM: Unknown
<220> FEATURE:
<223> OTHER INFORMATION: Mcl-1L DNA oligonucleotide

<400> SEQUENCE: 3
ttggctttgt gtccttggcg                                               20

<210> SEQ ID NO 4
<211> LENGTH: 20
<212> TYPE: DNA
<213> ORGANISM: Unknown
<220> FEATURE:
<223> OTHER INFORMATION: p53 DNA oligonucleotide

<400> SEQUENCE: 4
ccctgctccc ccctggctcc                                               20

<210> SEQ ID NO 5
<211> LENGTH: 23
<212> TYPE: DNA
<213> ORGANISM: Artificial Sequence
<220> FEATURE:
<223> OTHER INFORMATION: anti-p53 DNA oligonucleotide

<400> SEQUENCE: 5
gggcaccacc acactatgtc gaa                                           23

<210> SEQ ID NO 6
<211> LENGTH: 49
<212> TYPE: RNA
<213> ORGANISM: Artificial Sequence
<220> FEATURE:
<223> OTHER INFORMATION: anti p53 RNA oligonucleotide

<400> SEQUENCE: 6
gacuccagug guaaucuacu ucaagagagu agauuaccac uggagucuu               49

<210> SEQ ID NO 7
<211> LENGTH: 18
<212> TYPE: DNA
<213> ORGANISM: Escherichia coli RNA I

<400> SEQUENCE: 7
gcgatcgtct cggctcta                                                 18

<210> SEQ ID NO 8
<211> LENGTH: 18
<212> TYPE: DNA
<213> ORGANISM: Artificial Sequence
<220> FEATURE:

<223> OTHER INFORMATION: anti GNP oligonucleotide 2

<400> SEQUENCE: 8
ctctagcaga gcgcagat                                                    18

<210> SEQ ID NO 9
<211> LENGTH: 18
<212> TYPE: DNA
<213> ORGANISM: Unknown
<220> FEATURE:
<223> OTHER INFORMATION: anti-GFP oligonucleotide

<400> SEQUENCE: 9
ctgccgtcgc acgtcgag                                                    18

<210> SEQ ID NO 10
<211> LENGTH: 18
<212> TYPE: RNA
<213> ORGANISM: Artificial Sequence
<220> FEATURE:
<223> OTHER INFORMATION: antisense-GFP oligonucleotide

<400> SEQUENCE: 10
gacggcagcg ugcagcuc                                                    18

<210> SEQ ID NO 11
<211> LENGTH: 86
<212> TYPE: DNA
<213> ORGANISM: Artificial Sequence
<220> FEATURE:
<223> OTHER INFORMATION: sh-p53-template

<400> SEQUENCE: 11
taatacgact cactataggg acggcagcgt gcagctcgac tccagtggta atctacttca      60
agagagtaga ttaccactgg agtctt                                           86

<210> SEQ ID NO 12
<211> LENGTH: 97
<212> TYPE: DNA
<213> ORGANISM: Artificial Sequence
<220> FEATURE:
<223> OTHER INFORMATION: sh-Mcl-1L-template-1

<400> SEQUENCE: 12
taatacgact cactataggg acggcagcgt gcagctcccc cgggactggc tagttaaact      60
tcaagagagt ttaactagcc agtcccgttt ttggaaa                               97

<210> SEQ ID NO 13
<211> LENGTH: 97
<212> TYPE: DNA
<213> ORGANISM: Artificial Sequence
<220> FEATURE:
<223> OTHER INFORMATION: sh-Mcl-1L-template-2

<400> SEQUENCE: 13
taatacgact cactataggc tctagcagag ccgagatccc cgggactggc tagttaaact      60
tcaagagagt ttaactagcc agtcccgttt ttggaaa                               97

<210> SEQ ID NO 14
<211> LENGTH: 20
<212> TYPE: DNA
<213> ORGANISM: Artificial Sequence
<220> FEATURE:
<223> OTHER INFORMATION: T7-1 primer

<400> SEQUENCE: 14
ttaatacgac tcactatagg                                                    20

<210> SEQ ID NO 15
<211> LENGTH: 16
<212> TYPE: DNA
<213> ORGANISM: Artificial Sequence
<220> FEATURE:
<223> OTHER INFORMATION: sh-p53-R primer

<400> SEQUENCE: 15
aagactccag tggtaa                                                        16

<210> SEQ ID NO 16
<211> LENGTH: 21
<212> TYPE: DNA
<213> ORGANISM: Artificial Sequence
<220> FEATURE:
<223> OTHER INFORMATION: shMCL-1-R primer

<400> SEQUENCE: 16
ttaccaaaaa cgggactggc t                                                  21

<210> SEQ ID NO 17
<211> LENGTH: 20
<212> TYPE: DNA
<213> ORGANISM: Artificial Sequence
<220> FEATURE:
<223> OTHER INFORMATION: p53-F primer

<400> SEQUENCE: 17
agctttgagg tgcgtgtttg                                                    20

<210> SEQ ID NO 18
<211> LENGTH: 20
<212> TYPE: DNA
<213> ORGANISM: Artificial Sequence
<220> FEATURE:
<223> OTHER INFORMATION: p53-R primer;

<400> SEQUENCE: 18
tcagctctcg gaacatctcg                                                    20

<210> SEQ ID NO 19
<211> LENGTH: 20
<212> TYPE: DNA
<213> ORGANISM: Artificial Sequence
<220> FEATURE:
<223> OTHER INFORMATION: MCL-1L-F primer

<400> SEQUENCE: 19
tggtcgggga atctggtaat                                                    20

<210> SEQ ID NO 20
<211> LENGTH: 20
<212> TYPE: DNA
<213> ORGANISM: Artificial Sequence
<220> FEATURE:
<223> OTHER INFORMATION: MCL-1L-R primer

<400> SEQUENCE: 20
gtaaggtctc cagcgccttc                                                    20

<210> SEQ ID NO 21

```
<211> LENGTH: 22
<212> TYPE: DNA
<213> ORGANISM: Artificial Sequence
<220> FEATURE:
<223> OTHER INFORMATION: GAPDH-F primer

<400> SEQUENCE: 21
agccaaaagg gtcatcatct ct                                              22

<210> SEQ ID NO 22
<211> LENGTH: 19
<212> TYPE: DNA
<213> ORGANISM: Artificial Sequence
<220> FEATURE:
<223> OTHER INFORMATION: GAPDH-R primer

<400> SEQUENCE: 22
aggggccatc cacagtctt                                                  19

<210> SEQ ID NO 23
<211> LENGTH: 33
<212> TYPE: DNA
<213> ORGANISM: Artificial Sequence
<220> FEATURE:
<223> OTHER INFORMATION: Dz2208

<400> SEQUENCE: 23
catctcatga gcaacatcga tcggtccatc atg                                  33

<210> SEQ ID NO 24
<211> LENGTH: 38
<212> TYPE: DNA
<213> ORGANISM: Artificial Sequence
<220> FEATURE:
<223> OTHER INFORMATION: Antisense-p53-1

<400> SEQUENCE: 24
ctctagcaga gcgcagatcc ctgctccccc ctggctcc                             38

<210> SEQ ID NO 25
<211> LENGTH: 28
<212> TYPE: DNA
<213> ORGANISM: Artificial Sequence
<220> FEATURE:
<223> OTHER INFORMATION: GFP antisense DNA

<400> SEQUENCE: 25
gagctgcacg ctgccgtcaa aaaaaaaa                                        28

<210> SEQ ID NO 26
<211> LENGTH: 41
<212> TYPE: DNA
<213> ORGANISM: Artificial Sequence
<220> FEATURE:
<223> OTHER INFORMATION: Dz2208 DNAzyme bound to GFP antisense DNA

<400> SEQUENCE: 26
cgtgcagcca tctcatgagc aacatcgatc ggtccatcat g                         41

<210> SEQ ID NO 27
<211> LENGTH: 18
<212> TYPE: DNA
<213> ORGANISM: Artificial Sequence
<220> FEATURE:
<223> OTHER INFORMATION: antisense-RNAI oligonucleotide

<400> SEQUENCE: 27
```

-continued

```
ctctagcaga gcgcagat                                              18

<210> SEQ ID NO 28
<211> LENGTH: 20
<212> TYPE: DNA
<213> ORGANISM: Artificial Sequence
<220> FEATURE:
<223> OTHER INFORMATION: Luc-S1 oligonucleotides

<400> SEQUENCE: 28
gcgatctgca tctcaattag                                            20

<210> SEQ ID NO 29
<211> LENGTH: 44
<212> TYPE: DNA
<213> ORGANISM: Artificial Sequence
<220> FEATURE:
<223> OTHER INFORMATION: RNA I-Luc-S1 oligonucleotides

<400> SEQUENCE: 29
ctctagcaga gcgcagatcc ccccgcgatc tgcatctcaa ttag                 44

<210> SEQ ID NO 30
<211> LENGTH: 20
<212> TYPE: DNA
<213> ORGANISM: Artificial Sequence
<220> FEATURE:
<223> OTHER INFORMATION: Luc-AS1 oligonucleotides

<400> SEQUENCE: 30
gacggatccg ctgtggaatg                                            20

<210> SEQ ID NO 31
<211> LENGTH: 44
<212> TYPE: DNA
<213> ORGANISM: Artificial Sequence
<220> FEATURE:
<223> OTHER INFORMATION: RNA I-Luc-AS1 oligonucleotides

<400> SEQUENCE: 31
ctctagcaga gcgcagatcc ccccgacgga tccgctgtgg aatg                 44

<210> SEQ ID NO 32
<211> LENGTH: 57
<212> TYPE: DNA
<213> ORGANISM: Artificial Sequence
<220> FEATURE:
<223> OTHER INFORMATION: anti Mcl-1L RNA oligonucleotide

<400> SEQUENCE: 32
ccccggactg gctagttaac ttcaagagag tttaactagc cagtccgttt ttggaaa   57

<210> SEQ ID NO 33
<211> LENGTH: 19
<212> TYPE: RNA
<213> ORGANISM: Artificial Sequence
<220> FEATURE:
<223> OTHER INFORMATION: cleavage site of Dz2208

<400> SEQUENCE: 33
caugauggaa caugagaug                                             19

<210> SEQ ID NO 34
<211> LENGTH: 15
<212> TYPE: RNA
```

```
<213> ORGANISM: Artificial Sequence
<220> FEATURE:
<223> OTHER INFORMATION: cleavage site of Dz2208
<220> FEATURE:
<221> NAME/KEY: misc_feature
<222> LOCATION: (1)..(7)
<223> OTHER INFORMATION: n is a, c, g, or u
<220> FEATURE:
<221> NAME/KEY: misc_feature
<222> LOCATION: (10)..(15)
<223> OTHER INFORMATION: n is a, c, g, or u

<400> SEQUENCE: 34
nnnnnnnryn nnnnn                                                     15

<210> SEQ ID NO 35
<211> LENGTH: 29
<212> TYPE: DNA
<213> ORGANISM: Artificial Sequence
<220> FEATURE:
<223> OTHER INFORMATION: 10-23 DNAzyme
<220> FEATURE:
<221> NAME/KEY: misc_feature
<222> LOCATION: (1)..(7)
<223> OTHER INFORMATION: n is a, c, g, or t
<220> FEATURE:
<221> NAME/KEY: misc_feature
<222> LOCATION: (23)..(29)
<223> OTHER INFORMATION: n is a, c, g, or t

<400> SEQUENCE: 35
nnnnnnnggc tagctacaac gannnnnnn                                      29
```

US 8,871,509 B2

NANOPARTICLE-BASED GENE DELIVERY SYSTEMS

CROSS-REFERENCE TO RELATED APPLICATIONS

This application is the U.S. national stage filing under 35 U.S.C. §371 of international application PCT/KR2010/001679, filed Mar. 18, 2010, which claims benefit of Korean Patent Application No. 10-2010-0024120, filed Mar. 18, 2010, and Korean Patent Application No. 10-2009-0107234, filed Nov. 6, 2009.

BACKGROUND OF THE INVENTION

1. Field of the Invention

The present invention relates to a gene delivery system containing nanoparticles.

2. Description of the Related Art

Gene therapy is attractive as a clinical treatment for cancers and genetic disorders of both congenital and acquired origins [1]. Efficient gene delivery systems are central to the clinical treatment of genetic disorders and cancer and have attracted considerable attention in recent years [1]. The use of recombinant viruses as gene carriers was the focus of early studies due its high transfection efficiencies and levels of protein expressions [2]. However, these systems are critically limited because viral proteins trigger strong immune responses, which has resulted in a lack of FDA-approved products [3]. Additionally, viral delivery systems are limited in scale-up procedures [4]. As a result, numerous nonviral gene delivery systems such as cationic lipids, polymers, dendrimers, and peptides have been developed [5]. However, unlike, nonviral gene delivery systems exhibit significantly reduced transfection efficiencies compared to viral systems due to numerous extra- and intracellular obstacles. Therefore, many researchers continue to focus on designing safe and efficient viral delivery vectors.

Recently, nanomaterials, including carbon nanotubes and iron oxide, silica, and gold nanoparticles, have been intensively studied as alternative nonviral gene delivery systems [6]. Gold nanoparticles are attractive scaffolds for the creation of gene delivery systems because they are bioinert, nontoxic, and easily synthesized and functionalized [7]. Thus far, several strategies for gene delivery systems have been developed, including mixed monolayer protected gold nanoparticles, complexes of polymer and gold nanoparticles, double-stranded DNA functionalized gold nanoparticles, and single stranded DNA functionalized gold nanoparticles [8]. Single-stranded DNA functionalized gold nanoparticles developed by Mirkin et al. were a good gene delivery system and antisense [8f]. Moreover, these nanoparticles showed greater knockdown of gene expression, higher binding affinity for target DNA, higher immunity to nuclease, and lower cell toxicity than antisense DNA delivered by either Lipofectamine or Cytofectin.

However, the system could deliver only antisense DNA covalently cross-linked to gold nanoparticles, which needed to be individually synthesized for each gene of interest, procedures that are both time consuming and inconvenient.

Therefore, there has been demanded for a gene delivery system that can be used for delivery of any antisense DNA oligo without a need for the synthesis of the gold nanoparticles covalently linked to antisense DNA oligo specific to the gene of interest.

Throughout this application, various patents and publications are referenced and citations are provided in parentheses. The disclosure of these patents and publications in their entities are hereby incorporated by references into this application in order to more fully describe this invention and the state of the art to which this invention pertains.

DETAILED DESCRIPTION OF THIS INVENTION

The present inventors have made intensive researches to develop an effective gene delivery system for a material (e.g., oligo antisense DNAs specific to a target gene) which enables to inhibit the expression of a target gene without affecting normal cell physiology. As results, we have discovered a gene delivery system in which an universal binding partner is covalently linked to the surface of a nanomaterial followed by binding an inhibitory molecule or an inducible molecule having the sequence of the target gene of interest to be expressed as a binding counter-partner, contributing to inhibition or expression of the target gene in a more effective manner.

Accordingly, it is an object of this invention to provide a gene delivery system containing a nanomaterial.

It is another object of this invention to provide a method for deliver a cargo into cells, comprising contacting into cells a gene delivery system.

Other objects and advantages of the present invention will become apparent from the following detailed description together with the appended claims and drawings.

In one aspect of this invention, there is provided a gene delivery system, comprising: (a) a nanomaterial; (b) an oligonucleotide as an universal binding partner covalently linked to the surface of the nanomaterial; and (c) a cargo comprising (i) a complementary oligonucleotide containing a nucleotide sequence complementary to the universal binding partner as a binding counter-partner, and (ii) an inhibitory molecule having a nucleotide sequence complementary to a target gene of interest to be inhibited or an inducible molecule having a nucleotide sequence of a target gene of interest to be expressed.

In another aspect of this invention, there is provided a method for deliver a cargo into cells, comprising contacting into cells a gene delivery system, comprising: (a) a nanomaterial; (b) an oligonucleotide as an universal binding partner covalently linked to the surface of the nanomaterial; and (c) a cargo comprising (i) a complementary oligonucleotide containing a nucleotide sequence complementary to the universal binding partner as a binding counter-partner, and (ii) an inhibitory molecule having a nucleotide sequence complementary to a target gene of interest to be inhibited or an inducible molecule having a nucleotide sequence of a target gene of interest to be expressed.

The present inventors have made intensive researches to develop an effective gene delivery system for a material (e.g., oligo antisense DNAs specific to a target gene) which enables to inhibit the expression of a target gene without affecting normal cell physiology. As results, we have discovered a gene delivery system in which an universal binding partner is covalently linked to the surface of a nanomaterial followed by binding an inhibitory molecule or an inducible molecule having the sequence of the target gene of interest to be expressed as a binding counter-partner, contributing to inhibition or expression of the target gene in a more effective manner.

The gene delivery system of the present invention comprises (a) a nanomaterial; (b) an oligonucleotide as a universal binding partner; and (c) a cargo including (i) a complementary oligonucleotide as a binding counter-partner, and (ii) an inhibitory molecule having a nucleotide sequence complementary to a target gene of interest to be inhibited or an inducible molecule having a nucleotide sequence of a target gene of interest to be expressed.

The term "nanomaterial" used herein as a component of the gene delivery system refers to a material with the size range of 1-100 nm, preferably. The form and shape of the nanomaterial used in this invention includes, but not limited to, any material of a nano-scale size, for example, having a form such as a particle, a tube, a rod or a regular tetrahedron.

According to a preferable embodiment, the nanomaterial used in the present invention is a nanoparticle. The term "nanoparticle" used herein refers to a particle of various materials with the diameter range of preferably 8-100 nm, more preferably 10-50 nm and most preferably 12-14 nm. The nanoparticle includes, but not limited to, a material of a nano-scale size, for example including a nanocarbon, a metal nanoparticle, a metal oxide particle, a quantum dot, a polymer latex, a polymer nanosphere, and so forth. Practical examples of the metal particle include Au, Ag, Pd, Pt, Cu, Ni, Co, Fe, Mn, Ru, Rh, Os or Ir. The metal oxide particle indicates a compound represented by the formula $M_xO_y$ (M represents metal; O represents oxygen; and x and y represent an integer), for example including $Fe_2O_3$, $Ag_2O$, $TiO_2$ or $SiO_2$.

More preferably, the nanomaterial used in the present invention means a metal nanoparticle. The term "metal nanoparticle" used herein refers to, but not limited to, a metal particle with the diameter range of preferably 8-100 nm, more preferably 10-50 nm and most preferably 12-14 nm (e.g., gold, silver, platinum, palladium and iron), and also includes all nano-sized particles of which the group have metal properties. The small particle size enables to feasibly penetrate the nanoparticle of the present invention to a cell of interest (e.g., human cells), resulting in penetration of a gene delivery system into cells. Consequently, the ease penetration allows the gene delivery system of the present invention to suppress the expression of a target molecule in much more effective manner.

According to the most preferable embodiment, the nanomaterial used in this invention includes a metal nanoparticle. Gold nanoparticles with a form of stable particle have several advantages such as (a) easy fabrication, (b) flexible size and (c) high bioaffinity having the non-toxicity in the body compared to a heavy metal including manganese, aluminum, cadmium, lead, mercury, cobalt, nickel or beryllium.

For instance, the gold nanoparticle used in this invention may be prepared as follows: gold nanoparticles were prepared by reducing $HAuCl_4$ using each $HAuCl_4$ and sodium citrate as a gold donor and a reducing agent. In this regard, the size of gold nanoparticle may be controlled depending on the amount of citrate added. In other words, the size of gold nanoparticle is decreased as nucleation is greatly formed in proportion to increase in the additive amount of citrate.

Gold nanoparticles have a property binding to other material (e.g., compound) feasibly. However, it is very difficult to attach gold nanoparticles as a state of particle to the surface of particular materials or to maintain them in the suspension condition because the stability of gold nanoparticle is reduced in the diameter of above 100 nm. Therefore, the diameter of gold nanoparticle in the present invention is in a range of preferably 8-100 nm, more preferably 10-50 nm and most preferably 12-14 nm.

Preferably, the oligonucleotide as the universal binding partner in the present invention has an additive functionality to be covalently linked to nanoparticles. The additive functionality is placed at the end of the oligonucleotide.

More preferably, a thiol or amine group is bound to the end of the oligonucleotide as the universal binding partner. Much more preferably, the additive functionality is located in 3'-end, followed by preferably an alkyl group, for example including alkyl groups having a carbon atom of 1-20 (preferably, alkyl group having a carbon atom of 4-8) at 5'-direction.

Although the universal binding partner may be directly linked to a functionality portion, it is preferable that a linker (or a spacer) is introduced to a middle portion. The linker allows the universal binding partner to bind to nanoparticles at higher density, and also contributes to binding of the universal binding partner with the binding counter-partner in a feasible manner. The suitable linker includes oligonucleotide or polyether, and preferably oligo A nucleotide, oligo T nucleotide, oligo G nucleotide or oligo C nucleotide.

Thus, according to a preferable embodiment, the universal binding partner has a structure of "3'-SH (or $NH_2$)-linker-oligonucleotide-5'", and more preferably "3'-SH (or $NH_2$)-alkyl-linker-oligonucleotide-5'"

According to a preferable embodiment, the oligonucleotide as the universal binding partner in the present invention includes a non-human nucleotide sequence. More preferably, the oligonucleotide as the universal binding partner is derived from animals except for viruses, prokaryotes, fungi, marine biota, plants or human, and may include nucleotide sequences absent in human cells. For example, the oligonucleotide as the universal binding partner includes a sequence derived from GFP (green fluorescence protein), and more preferably GFP variants, a nucleotide sequence derived from EGFP (enhanced green fluorescence protein). The present invention exhibits no effect on gene expression where the gene delivery system is introduced into human cells using non-human nucleotide sequences. In this reason, the present invention plays a role in selective inhibition only on a target gene expression.

The length of the oligonucleotide as the universal binding partner is not particularly limited, and is composed of preferably 3-100 nucleotide, more preferably 10-50 nucleotide, much more preferably 15-30 nucleotide, and most preferably 19-21 nucleotide.

The universal oligonucleotide may be modified at above one or more positions of base, sugar or backbone to enhance its efficacy (De Mesmaeker et al., *Curr Opin Struct Biol.*, 5(3): 343-55, 1995).

The term "binding counter-partner" used herein means an oligonucleotide having a sequence complementary to the universal binding partner or a homology at above ratio enough to hybridization.

According to a preferable embodiment, the complementary oligonucleotide as the binding counter-partner is composed of 3-100 nucleotide, more preferably 10-50 nucleotide, much more preferably 15-30 nucleotide, and most preferably 19-21 nucleotide.

The term "inhibition of target gene expression" of step (c) used herein refers to elimination or suppression of mRNA and/or protein level produced by target gene, e.g., mediated by RNA interference (RNAi) through cleavage of mRNA.

The term "target gene of interest to be inhibited" used herein means a gene or oligonucleotide to undergo expression inhibition in cells (preferably, animal cells, and more preferably, human cells). Preferably, the target gene of interest to be inhibited includes, but not limited to, oncogenes (e.g., c-myc, N-myc, L-myc, c-jun, jun-B, jun-D, c-fos, fos-B, ets-1, ets-2, myb, erbA, rel, ski, spi-1, evi-1, Ha-ras, Ki-ras, N-ras, erbB-1, erbB-2, erbB-2/neu, src, fms, mos, abl, ros, raf, yes, fps, trk, sis, p53, Adeno E1A, Polyoma large T, Papilloma E7, SV40 large T), apoptosis-inducible genes (e.g., caspase-8, caspase-9, Bcl-2, Mcl-1L) or immune disease-related genes (e.g., IFN-γ, IL-8, TNF-α, IL-1), which are expressed by introduction into the human cells intracellularly or extracellularly (e.g., virus or bacterium). In addition, the target gene or oligonucleotide includes single strand or double strand nucleotides.

According to a preferable embodiment, the present invention has an excellent efficiency on inhibition of p53 and Mcl-1L expression which are cancer and apoptosis-related genes.

The inhibitory molecule of this invention is linked to the binding counter-partner of the step (c) and in intracellular introduction of the gene delivery system, the activity of target gene may be much more remarkably suppressed by inhibition of target gene expression.

The term "complementary" used in the present invention comprehensively includes not only 100% complementarity, but also incomplete complementarity to what extent target gene expression may be inhibited, and refers to preferably 90% complementarity, more preferably 98% complementarity and most preferably 100% complementarity. The term "completely complementary" used in the present invention is particularly described for expression of 100% complementarity.

Preferably, the inhibitory molecule has a nucleotide sequence complementary to a partial sequence of the target gene to be inhibited. The term "target gene" used herein in conjunction of inhibition of gene expression means a regulatory sequence plus CDS (coding sequence) of target gene. For example, the inhibitory molecule may have a nucleotide sequence complementary to a regulatory sequence (e.g., promoter or enhancer) of the target gene or a partial sequence of the regulatory sequence. Alternatively, the inhibitory molecule may have a nucleotide sequence complementary to a partial sequence of CDS of the target gene. Furthermore, the inhibitory molecule may have a nucleotide sequence complementary to a partial sequence of the regulatory sequence and a partial sequence of CDS of the target gene.

The term "antisense oligonucleotide" used herein is intended to refer to nucleic acids, preferably, DNA, RNA or its derivatives, that are complementary to the base sequences of a target mRNA, characterized in that they bind to the target mRNA and interfere its translation to protein. The antisense oligonucleotide of the present invention refers to DNA or RNA sequences which are complementary to a target gene, characterized in that they bind to the target gene mRNA and interfere its translation to protein, translocation into cytoplasm, or essential activities to other biological functions. The length of antisense oligonucleotide is in a range of 6-100 nucleotides, preferably 8-60 nucleotides, and more preferably 10-40 nucleotides.

The antisense oligonucleotide may be modified at above one or more positions of base, sugar or backbone (De Mesmaeker et al., *Curr Opin Struct Biol.*, 5(3): 343-55 (1995)). The oligonucleotide backbone may be modified by phosphothioate, phosphotriester, methyl phosphonate, single chain alkyl, cycloalkyl, single chain heteroatomic, heterocyclic bond between sugars, and so on. In addition, the antisense oligonucleotide may include one or more substituted sugar moieties. The antisense oligonucleotide may include a modified base. The modified base includes hypoxanthine, 6-methyladenine, 5-me pyrimidine (particularly, 5-methylcytosine), 5-hydroxymethylcytosine (HMC), glycosyl HMC, gentobiosyl HMC, 2-aminoadenine, 2-thiouracil, 2-thiothymine, 5-bromouracil, 5-hydroxymethyluracil, 8-azaguanine, 7-deazaguanine, N6(6-aminohexyl)adenine, 2,6-diaminopurine, and so on.

The term "aptamer" used herein refers to an oligonucleotide (generally, RNA molecule) linked to a specific target. Preferably, "aptamer" used herein means an oligonucleotide aptamer (for example, RNA aptamer). General descriptions of aptamer are described in Bock L C et al., *Nature* 355 (6360): 564-6 (1992); Hoppe-Seyler F, Butz K "Peptide aptamers: powerful new tools for molecular medicine". *J Mol Med.* 78 (8): 426-30 (2000); Cohen B A, Colas P, Brent R. "An artificial cell-cycle inhibitor isolated from a combinatorial library". *Proc Natl Acad Sci USA.* 95 (24): 14272-7 (1998).

The term "siRNA" used herein refers to a short double strand RNA that enables to mediate RNA interference via cleavage of mRNA. The siRNA of the present invention may consist of a sense RNA strand having a sequence corresponding to a target gene and an antisense RNA strand having a sequence complementary to the target gene. The siRNA to inhibit expression of a target gene provides effective gene knock-down method or gene therapy method.

The siRNA of this invention is not restricted to a RNA duplex of which two strands are completely paired and may comprise non-paired portion such as mismatched portion with non-complementary bases and bulge with no opposite bases. The overall length of the siRNA is 10-100 nucleotides, preferably 15-80 nucleotides, and more preferably, 20-70 nucleotides. The siRNA may comprise either blunt or cohesive end so long as it enables to inhibit the target gene expression via RNAi effect. The cohesive end may be prepared in 3'-end overhanging structure or 5'-end overhanging structure. The base number protruded is not particularly limited, for example 1-8 bases, preferably 2-6 bases.

The full-length of siRNA molecule in the present invention may be calculated by the sum of a short nucleotide sequence consisting of double strand in a central portion and single strand protruded at both ends. In addition, siRNA may comprise low molecular weight RNA (for example, tRNA, rRNA, natural RNA molecule such as viral RNA or artificial RNA molecule) in the protruded portion of one end to the extent that it enables to maintain an effect on the inhibition of target gene expression. The terminal structure of siRNA is not demanded as cut structure at both ends, and one end portion of double strand RNA may be stem-and-loop structure linked by a linker RNA. The length of linker is not restricted where it has no influence on the pair formation of the stem portion.

In the present invention, the term "specific" or "distinct" used herein refers to a capability of inhibiting or promoting only a target gene expression without interfering other gene expression in the cell. The siRNA of this invention includes an antisense RNA strand which contains a sequence complementary to a target gene or target nucleotide and is applicable to the target gene in a specific manner.

The term "shRNA" means a single strand nucleotide consisting of 50-70 bases, and forms stem-loop structure in vivo. Long RNA of 19-29 nucleotides is complementarily base-paired at both directions of loop consisting of 5-10 nucleotides, forming a double-stranded stem.

The term "miRNA (microRNA)" functions to regulate gene expression and means single strand RNA molecule composed of 21-23 nucleotides in full-length. The miRNA is an oligonucleotide which is not expressed intracellularly, and forms a short stem-loop structure. The miRNA has a whole or partial complementarity to one or two or more mRNAs (messenger RNA), and the target gene expression is suppressed by the complementary binding of miRNA to the mRNA.

The term "ribozyme" refers to a RNA molecule having an activity of an enzyme which recognizes and restricts a base sequence of a specific RNA. The ribozyme is a base sequence complementary to transfer RNA strand as target and consists of a binding portion capable of specifically binding with the target nucleotide sequence and an enzymatic portion to restrict target RNA.

The term "DNAzyme" refers to a single-strand DNA molecule with enzymatic activity. DNAzyme consisting of 10-23 nucleotide sequence (10-23 DNAzyme) may restrict a specific site of RNA strand under physiological conditions. 10-23 DNAzyme may cleave any portion which is randomly protruded between purine and pyrimidine without pairs. 10-23 DNAzyme is as follows (SEQ ID NO:35): (a) a conserved catalytic domain of enzyme consisting of 15-nucleotide sequence; and (b) RNA substrate binding domain consisting of 7-8 nucleotide sequence placed at both ends of the catalytic domain.

The term "PNA (peptide nucleic acid)" means a molecule having the characteristics of both nucleic acid and protein, which is capable of complementarily binding to DNA or RNA. PNA was first reported in 1999 as similar DNA in which nucleobases are linked via a peptide bond (Nielsen P E, Egholm M, Berg R H, Buchardt O, "Sequence-selective recognition of DNA by strand displacement with a thymine-substituted polyamide", Science 1991, Vol. 254: pp 1497-1500). PNA is absent in the natural world and artificially synthesized through a chemical method. PNA is reacted with a natural nucleic acid having a complementary base sequence through hybridization response, forming double strand. In the double strand with the same length, PNA/DNA and PNA/RNA double strand are more stable than DNA/DNA and DNA/RNA double strand, respectively. The form of repeating N-(2-aminoethyl)-glycine units linked by amide bonds is commonly used as a basic peptide backbone. In this context, the backbone of peptide nucleic acid is electrically neutral different from that of natural nucleic acids having negative charge. Four bases of nucleic acid present in PNA are almost the same to those of natural nucleic acid in the respect of spatial size and distance between nucleobases. PNA has not only a chemical stability compared with natural nucleic acid, but also a biological stability due to no degradation by a nuclease or protease.

According to a preferable embodiment, the inhibitory molecule having the sequence complementary to the target gene of interest to be suppressed in the step (c) of the present invention includes antisense oligonucleotide, aptamer, siRNA (small interfering RNA), shRNA (short hairpin RNA), miRNA (microRNA), ribozyme, DNAzyme or PNA (peptide nucleic acid), more preferably antisense oligonucleotide, aptamer, siRNA, shRNA or DNAzyme.

The inducible molecule having the sequence of the target gene of interest to be expressed in this invention is linked to the binding counter-partner in the step (c), and permits to effectively facilitate target gene expression through introduction of gene delivery system into cells.

According to a preferable embodiment, the inducible molecule includes RNA or DNA.

Preferably, the inducible molecule in this invention is an expression construct containing (i) a promoter, and (ii) a CDS (coding sequence) of a target gene of interest to be expressed operatively linked to the promoter, and more preferably (i) a promoter, (ii) a CDS (coding sequence) of a target gene of interest to be expressed operatively linked to the promoter and (iii) a polyadenylation sequence.

The term "operatively linked" refers to functional linkage between a nucleic acid expression control sequence (such as a promoter, signal sequence, or array of transcription factor binding sites) and a second nucleic acid sequence, wherein the expression control sequence affects transcription and/or translation of the nucleic acid corresponding to the second sequence.

According to the present invention, the promoter used in the expression construct as the inducible molecule includes, but not limited to, TERT promoter, U6 promoter, H1 promoter, CMV (cytomegalovirus) promoter, the adenovirus late promoter, the vaccinia virus 7.5K promoter, SV40 promoter, HSV tk promoter, RSV promoter, EF1 alpha promoter, metallothionein promoter, beta-actin promoter, human IL-2 gene promoter, human IFN gene promoter, human IL-4 gene promoter, human lymphotoxin gene promoter, human GM-CSF gene promoter, inducible promoter, cancer cell-specific promoter (for example, PSA promoter, PSMA promoter, CEA promoter, E2F promoter and AFP promoter) or tissue-specific promoter (for example, albumin promoter).

According to the present invention, the polyadenylation sequence useful in the expression construct includes, without limitation, bovine growth hormone terminator (Gimmi, E. R., et al., *Nucleic Acids Res.*, 17: 6983-6998 (1989)), SV40-derived polyadenylation sequence (Schek, N., et al., *Mol. Cell Biol.*, 12: 5386-5393 (1992)), HIV-1 polyA (Klasens, B. I. F., et al., *Nucleic Acids Res.*, 26: 1870-1876 (1998)), β-globin polyA (Gil, A., et al., *Cell*, 49: 399-406 (1987)), HSV TK polyA (Cole, C. N. and T. P. Stacy, Mol. Cell. Biol. 5: 2104-2113 (1985)) or poliomavirus polyA (Batt, D. B. and G. G. Carmichael, *Mol. Cell. Biol.*, 15: 4783-4790 (1995)).

The term "target gene of interest to be expressed" used herein means a gene or oligonucleotide desirable to express in the cells (preferably, animal cells, and more preferably, human cells). Preferably, the target gene of interest to be expressed includes a gene (for example, luciferase gene) derived from human or other sources, or a therapeutic transgene.

Preferably, the therapeutic transgene includes tumor suppressor genes, antigenic genes, cytotoxic genes, cytostatic genes, apoptotic genes or anti-angiogenic genes.

The term "therapeutic transgene" used herein refers to a nucleotide sequence which exhibits a therapeutical efficacy corresponding to its expression in the cell, including tumor suppressor genes, antigenic genes, cytotoxic genes, cytostatic genes, apoptotic genes or anti-angiogenic genes, but not limited to.

The term "tumor suppressor gene" used herein means a nucleotide sequence which may inhibit a tumor phenotype depending on its expression in the cell, or induce apoptosis. The tumor suppressor gene useful in the present invention includes p53 gene, APC gene, DPC-4/Smad4 gene, BRCA-1 gene, BRCA-2 gene, WT-1 gene, retinoblastoma gene (Lee et al., *Nature*, 329: 642 (1987)), MMAC-1 gene, adenomatous-polyposis coil protein (U.S. Pat. No. 5,783,666), deleted in colorectal cancer (DCC) gene, MMSC-2 gene, NF-1 gene, nasopharyngeal carcinoma tumor suppressor gene that maps at chromosome 3p21.3 (Cheng et al. *Proc. Nat, Acad. Sci*, 95: 3042-3047 (1998)), MTS1 gene, CDK4 gene, NF-1 gene, NF-2 gene or VHL gene.

The term "antigenic gene" used herein refers to a nucleotide sequence which is expressed in the target cells to produce a cell surface antigenic protein recognized in the immune system. The exemplary antigenic gene includes carcinoembryonic antigen (CEA) and p53 (Levine, A., PCT publication No. WO 94/02167). The antigenic gene may be linked to type I MHC antigen for feasible recognition via immune system.

The term "cytotoxic gene" used herein refers to a nucleotide sequence which represents a cytotoxic effect on the cells depending on its expression. The example of the cytotoxic gene includes a nucleotide sequence encoding pseudomonas exotoxin, ricin toxin, diphtheria toxin, and so forth.

The term "cytostatic gene" used herein refers to a nucleotide sequence which halts progress in cell cycle according to its expression. The exemplary cytostatic gene includes, but not limited to, p21, retinoblastoma gene, E2F-Rb fusion protein gene, gene encoding a cyclin-dependent kinase inhibitor (for example, p16, p15, p18 and p19) or growth arrest specific homeobox (GAX) gene (PCT publication No. WO 97/16459 and WO 96/30385).

The term "apoptotic gene" used herein refers to a nucleotide sequence of which the expression induces a programmed cell death. The example of pro-apoptotic gene includes p53, adenovirus E3-11.6K (derived from Ad2 and Ad5) or adenovirus E3-10.5K (derived from Ad), adenovirus E4 gene, p53 pathway genes or genes encoding caspases.

The term "anti-angiogenic gene" used herein refers to a nucleotide sequence of which the expression induces an extracellular secretion of anti-angiogenic factor. The example of anti-angiogenic factor includes angiostatin, vascular endothelial growth factor (VEGF) inhibitor such as Tie 2 (*PNAS*, 95: 8795-8800 (1998)) or endostatin.

The present invention may be applied to various cells to deliver a cargo into cells. For instance, the cells used in the present invention include animal cells, more preferably mammalian cells, and much more preferably human, mouse, rat, bovine, pig, horse, rabbit or goat cells. In addition, the cells used in the present invention include somatic cells, reproductive cells, immune cells, embryonic stem cells, adult stem cells, iPCs (induced pluripotent stem cells) or precursor cells. Moreover, the present invention may be applied to all tumor cells, cancer cell lines and primary cultured cells.

The features and advantage of the present invention are summarized as follows:

(i) The present invention provides a gene delivery system containing nanoparticles. In more detail, the present invention provides a gene delivery system containing (a) a nanomaterial; (b) an oligonucleotide covalently linked to the surface of the nanomaterial as an universal binding partner; and (c) a cargo comprising (i) a complementary oligonucleotide containing a sequence complementary to the binding partner as a binding counter-partner, and (ii) an inhibitory molecule having a sequence complementary to a target gene of interest to be suppressed or an inducible molecule having a sequence of a target gene of interest to be expressed.

(ii) The present invention is a gene delivery system capable of feasibly deliver aptamer, siRNA, shRNA, miRNA, ribozyme, DNAzyme, PNA or gene as well as antisense oligonucleotide into the cells.

(iii) In addition, the present invention is more efficient than the commercially available gene transfer reagent (for example, Lipofectamine 2000) in respect to the degree of knockdown of target protein expression.

BRIEF DESCRIPTION OF THE DRAWINGS

FIG. 4 represents knockdown of gene expression by Au NP-GDS-antisense oligo complexes in different cell lines.

FIG. 7b represents a nucleotide sequence of AuNP-oligo (SEQ ID NO:7) and antisense oligo (SEQ ID NO:24) linked to gold nanoparticles used in knockdown of p53 expression.

FIGS. 8b-8c represent a nucleotide sequence (FIG. 8b) of AuNP-oligo and (SEQ ID NO:1) and p53 shRNA (SEQ ID NO:27and SEQ ID NO:6) linked to gold nanoparticles used in knockdown of p53 expression and a synthetic process of p53 shRNA (FIG. 8c).

FIG. 9a is a histogram showing the expression of luciferase gene delivered using AuNP-αRNA I. FIG. 9c shows a result synthesizing three-type PCR DNA using four oligos and pGL3-Control (SEQ ID NO:8and SEQ ID NOs:28-31).

Figure 1:
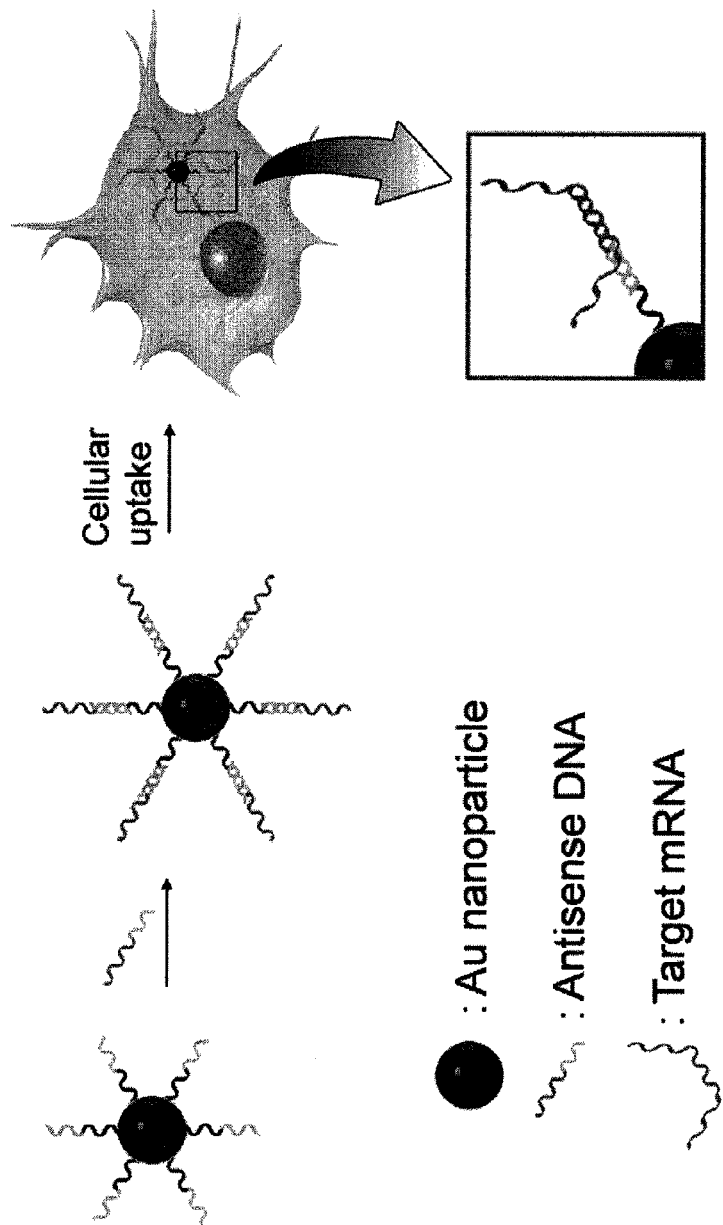
FIG. 1 schematically represent a single-stranded DNA functionalized gold (Au) nanoparticle-antisense.

The present invention will now be described in further detail by examples. It would be obvious to those skilled in the art that these examples are intended to be more concretely illustrative and the scope of the present invention as set forth in the appended claims is not limited to or by the examples.

EXAMPLES

The percentages given below for solid in solid mixture, liquid in liquid, and solid in liquid are on a wt/wt, vol/vol and wt/vol basis, respectively, unless specifically indicated otherwise.

Materials and Methods
Preparation of Single-Stranded DNA Functionalized AuNP-shRNA Conjugates AuNP•αGFP or AuNP•RNA I (10 nM) were mixed with shRNA in annealing buffer (1× phosphate-buffered saline containing 0.3 M NaCl) by gentle shaking for 10 min, incubated at 55° C. for 10 min, and cooled to 4° C. for about 1 hr. The resulting conjugates were spun down at 12,000×g for 10 min, the supernatant was removed, and the conjugate pellet was resuspended in DMEM medium. This precipitation and resuspension step was carried out three times. The conjugates (10 nM) was added to a tissue culture media, such that the final concentration was 1 nM.

Synthesis of shRNA In Vitro

ShRNA was synthesized from synthetic oligonucleotieds containing the sequence of T7 promoter followed by the sequence of short haripin structure of p53 and MCL-1 using the MEGAshortscript™ kit (Ambion, USA) according to the manufacturer's instruction. DNA templates were prepared by amplifying oligonucleotides using PCR. For the synthesis of shRNA-p53 and shRNA-Mcl1 that were intended to be hybridized to AuNP•αGFP, sh-p53-template (5'-TAATACGACTCACTATAGGGACGGCAGCGTG-CAGCTCGACTCCAGTGGTAATCTACT TCAAGAGAG-TAGATTACCACTGGAGTCTT (SEQ ID NO:11); T7 promoter is underlined) and sh-Mcl-1L-template-1 5'TAATACGACTCACTATAGGGACG-GCAGCGTGCAGCTCCCCCGGGACTGGCTAGTT AAACTTCAAGAGAGTTTAACTAGC-CAGTCCCGTTTTTGGAAA (SEQ ID NO:12); T7 promoter is underlined) were used, respectively. For the synthesis of shRNA-Mcl1 that was intended to be hybridized to AuNP•αRNA I, sh-Mcl-1L-template-2 (5'TAATACGACT-CACTATAGGCTCTAGCAGAGCCGAGATC-CCCGGGACTGGCTAGTT AAACTTCAAGAGAGTT-TAACTAGCCAGTCCCGTTTTTGGAAA (SEQ ID NO13); T7 promoter is underlined). The PCR primers used were T7-1 (5'-TTAATACGACTCACTATAGG-3'(SEQ ID NO:14))and sh-p53-R (5'-AAGACTCCAGTGGTAA-3'), (SEQ ID NO:15)), shMCL-1-R (5'-TTACCAAAAACGG-GACTGGCT-3'(SEQ ID NO:16). Synthesized shRNAs were purified with illustra™ MicroSpin™ G-50 columns (GE; Little Chalfont, Buckinghamshire, UK)

Western Blot Analysis

HEK293 (4.5×10$^5$) or HeLa cells (3.0×10$^5$) were incubated with short hairpin RNA functionalized with gold-nanoparticles in six-well dishes. Cell were lysed in NP-40 lysis buffer (50 mM Tris-HCl, pH 8.0, 0.15 M NaCl, and 1% NP-40) containing 10% protease inhibitor cocktail (Sigma). For quantitative protein analysis, a standard curve was established with the standard BSA solution (Pierce, Rockford, Ill., USA), and cell lysates containing equal amounts of total protein were separated by 10% polyacrylamide gel and transferred onto nitrocellulose membrane and western blot analyses were performed. Anti-p53 monoclonal and anti-MCL1-L polyclonal antibodies (both from Santa Cruz Biotechnology, Santa Cruz, Calif., USA) were used to detect p53 and MCL-1L, respectively.

Semi-Quantitative RT PCR

Total RNA was extracted from the cell lines with TRI Reagent® Solution (Ambion) according to the manufacturer's instructions. Synthesis of cDNA was performed using with 3 μg of the total RNA using the PrimScript™ 1st-Strand Cdna Synthesis kit (Takara; Otsu, Shiga, Japan). PCR was carried out in a total volume of 20 μl, using 2 μl of RT reaction. The PCR products were analyzed in 2% agarose gels. Primers used for p53 were p53-F (5'-AGCTTTGAGGTGCGT-GTTTG (SEQ ID NO17) and p53-R (5'-TCAGCTCTCG-GAACATCTCG), (SEQ ID NO:18)), and MCL-1L-F (5'-TGGTCGGGGAATCTGGTAAT (SEQ ID NO:19)) and MCL-1L-R (5'-GTAAGGTCTCCAGCGCCTTC (SEQ ID NO:20))for MCL-1L and GAPDH-F (5'-AGC-CAAAAGGGTCATCATCTCT) (SEQ ID NO:21))and GAPDH-R (5'-AGGGGCCATCCACAGTCTT) for loading control.

Figure 13B:
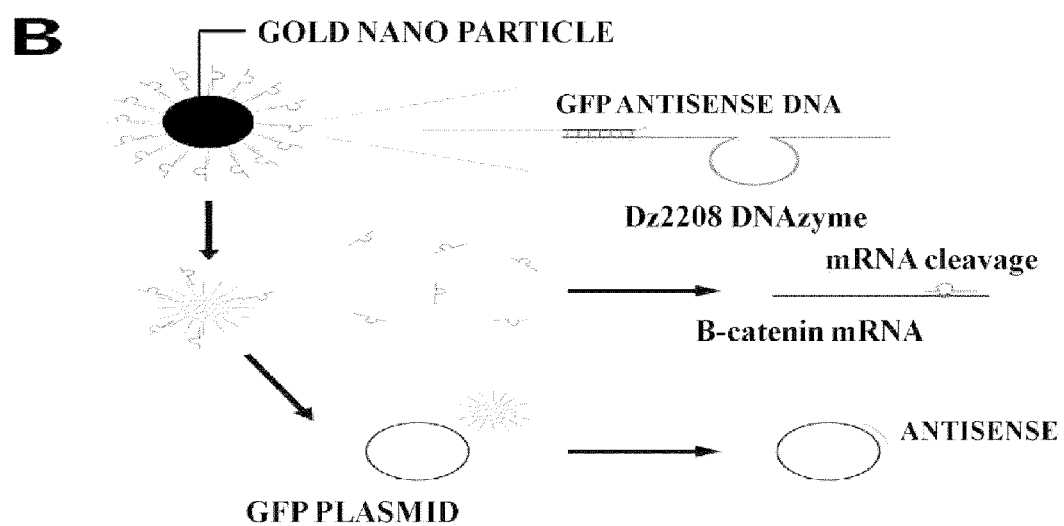
FIG. 13 represents preparation of DNAzyme annealed gold nano particles. (A) General sequence of RNA-cleaving DNAzyme is shown in the box (SEQ ID NOs:34 and 35). DNAzyme cleaves any purine (R) and pyrimidine (Y) junction in RNA that is complementary to the DNAzyme sequence. At a position of 2208$^{th}$ base of β-catenin mRNA is chosen for cleavage with DNAzyme (Dz2208) (SEQ ID NO:33). (B) Scheme of action by the DNAzyme annealed to GFP antisense oligonucleotide-conjugated gold nano particles. (C) Sequence of DNAzyme (SEQ ID NO:25) annealed to GFP antisense oligonucleotide (SEQ ID NO:26).

Preparation of DNAzyme-Annealed Gold Nano Particle and Gel-Shift Analysis

β-catenin mRNA-cleaving DNAzyme (sequence shown in FIG. 13) was constructed and its 5'-terminal sequence was designed to be annealed to the GFP antisense oligonucleotide conjugated to gold nano particle (FIG. 13). To anneal the DNAzyme to the GFP antisense oligonucleotide-conjugated gold nano particles, the following procedure was carried out. 1 ml of gold nano particle solution (36.5 nM) was centrifuged at 13,000 rpm at 4° C. for 40 min. Supernatant was removed and the pellet was rapidly mixed with 1 ml of 1% BSA solution in saline-free phosphate buffer (pH. 7.5). After the pellet solution was incubated for 30 min at room temperature, it was centrifuged at 13,000 rpm at 4° C. for 40 min. The pellet containing gold nano particles was resuspended with 300 μl of saline-free phosphate buffer (pH. 7.5) to be 120 nM and stored at 4° C. for further use. 10 μl of DNAzyme oligonucleotide (10 μM) was mixed with various amounts (at desired concentration, shown in FIG. 14) of the BSA-protected gold nano particles which were prepared as above. The mixing solution was supplemented with 20 mM MgCl$_2$ and Tris/HCl (20 mM, pH 7.5). For annealing of DNAzyme to the gold nano particles, the DNA mixed solution was heated at 95° C.

for 2 min, 42° C. for 10 min, and slowly cooled to the room temperature. These DNAzyme-annealed gold nano particles are ready for use.

Figure 14A:
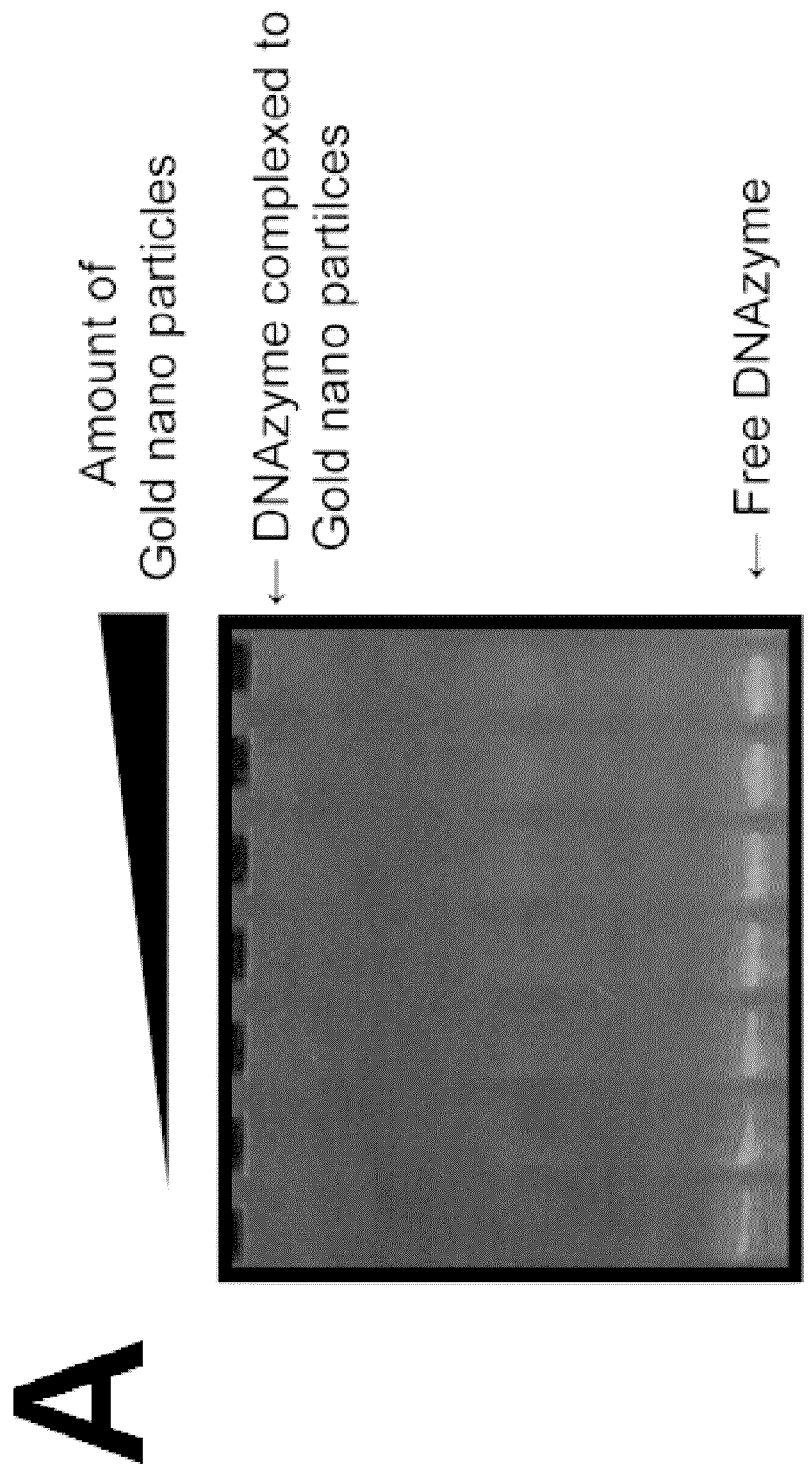
FIG. 14 indicates that DNAzyme annealed gold nano particles reduces target gene expression in cells. (A) Extent of DNAzyme annealing to the gold nano particles was analyzed with native poly acrylamide gel electrophoresis (15%). See text for details. (B) Transfection of the DNAzyme annealed gold nano particles into GFP-expressing cells was performed. At 24 hrs after transfection green fluorescence emitted from the cells were measured with the fluorescence microscope. Note the decrease in green fluorescence in cells after transfection with the gold nano particles. (C) Colon cancer cells transfected with Dz2208-annealed gold nano particles (1.0 and 10. nM) was lysed and analyzed for β-catenin protein expression with Western blot assay.

The extent of DNAzyme annealing to the gold nano particles was analyzed with native (nondenaturing) poly acrylamide gel electrophoresis (15%). Fixed amount of DNAzyme (10 µM) was mixed with increasing amount of the BSA-protected nano particles (0, 0.5, 1, 2, 4, 10, and 15 µl). Gel was run for 2 hrs and stained with ethidium bromide for the detection of DNA under UV transilluminator (FIG. 14A).

Cell Culture, Transfection of Oligonucleotides, and Fluorescence Microscopy

Figure 14B:
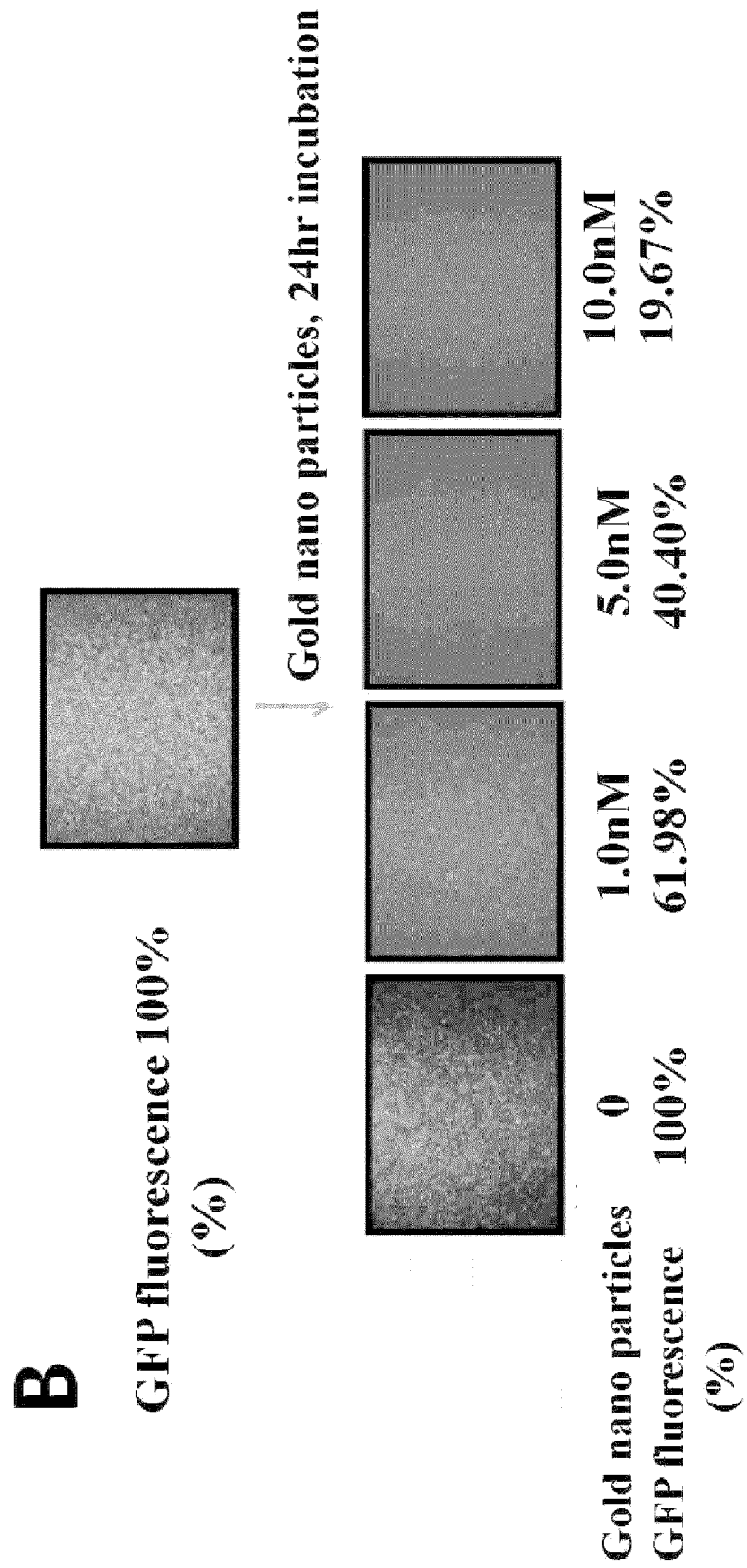

Colon cancer cell line SW480 were obtained from the American Type Culture Collection (Manassas, Va., USA), and maintained in DMEM supplemented with 10% FBS, 120 µg penicillin/ml, and 200 µg streptomycin/ml in a 37° C. incubator with 5% $CO_2$ humidified air. Approximately, $6 \times 10^4$ cells were plated per 12-well plate in media containing 10% fetal bovine serum to give 50-60% confluence. Cells were transfected with Green Fluorescence Protein (GFP) expression plasmid DNA using the Lipofectamine™ 2000 (Invitrogen, Carlsbad, Calif., USA) according to the manufacturer's instructions. The transfection reagent was completely removed by exchanging culture media. At 24 hrs after transfection of GFP plasmid, transfections of antisense DNAzyme oligonucleotides were carried out with the GFP antisense oligonucleotide-modified gold nano particles. Transfection of the DNAzyme was performed using the gold nano particles to a desired concentration of each oligonucleotide. At 24 hrs after transfection of the DNAzyme-annealed gold nano particles, green fluorescence emitted from the cells were measured with the fluorescence microscope (FIG. 14B). After monitoring the green fluorescence, the cells were harvested and lysed in lysis buffer (20 mM Tris-HCl, pH 8.0, 0.1% NP-40, 20 mM EDTA, 10% glycerol, 10 mM KCl) for Western blot analysis.

Lysed cell proteins were separated by 10% SDS-PAGE and transferred to a nitrocellulose membrane (Whatman). The membranes were blocked with 5% nonfat milk and probed with anti-β-catenin (1:500; Santa Cruz Biotechnology), and anti-β-actin (1:1000; Sigma). After washing, the membranes were incubated with horseradish peroxidase-conjugated anti-mouse IgG antibody (Santa Cruz Biotechnology) at a 1:3000 dilution for 1 hr at room temperature, then developed using the enhanced chemiluminescence system (Intron Biotechnology, Seoul, Korea) (FIG. 14C).

Example 1

Preparation of AuNP GDS-Mcl-1L-AS Conjugates

We describe the development of a gene delivery system showing the use of single-stranded DNA functionalized gold nanoparticles (henceforth referred to as "gold nanoparticle gene delivery system (AuNP GDS)") as a general platform for loading and delivering antisense DNA specific to any gene of interest.

To prepare single-stranded DNA functionalized gold nanoparticles as AuNP GDS, we used an oligonucleotide (5'-CTCGACGTGCGACGGCAG-3') bearing a sequence complementary to the coding region (bases 1198 to 1215; 5'-GAGCTGCACGCTGCCGTC-3'(SEQ ID NO 1)) of EGFP (anti-EGFP oligo) because it has been shown to be effective in the delivery and silencing the expression of EGFP in human tissue cultures without interfering with expression of human genes other than egfp.[9] AuNP GDS was prepared by functionalizing 13 nm gold nanoparticle with the thiolated anti-EGFP oligo.[10] To test whether the AuNP GDS can be used as a gene delivery system, anti-EGFP oligo-functionalized gold nanoparticles were annealed with antisense DNA (AuNP GDS-AS) having a complementary sequence to the anti-EGFP oligo DNA and a sequence specific to Mcl-1L (myeloid cell leukemia-1 long) gene, and the resulting conjugates were applied to HeLa cells (Human Cervix Carcinoma, Korean Cell Line Bank). The gene mcl-1L encodes an antiapoptotic Bcl-2 family protein which was discovered as an early induction gene during leukemia cell differentiation. To verify the delivery of the antisense oligo into the cell, we used the oligo labeled with FITC at the 3'-end for producing AuNP GDS-Mcl1-1L-AS-FITC conjugates (COSMO GENETECH Co. LTD, Seoul, Korea). Antisense DNA to the Mcl-1L contained a sequence complementary to AuNP GDS followed by a 20 nucleotide-sequence complementary to an internal coding region (bases 576 to 595; 5'-TTGGCTTTGT-GTCCTTGGCG-3')(SEQ ID NO:3)) of the Mcl-1L mRNA [11].

Figure 2:
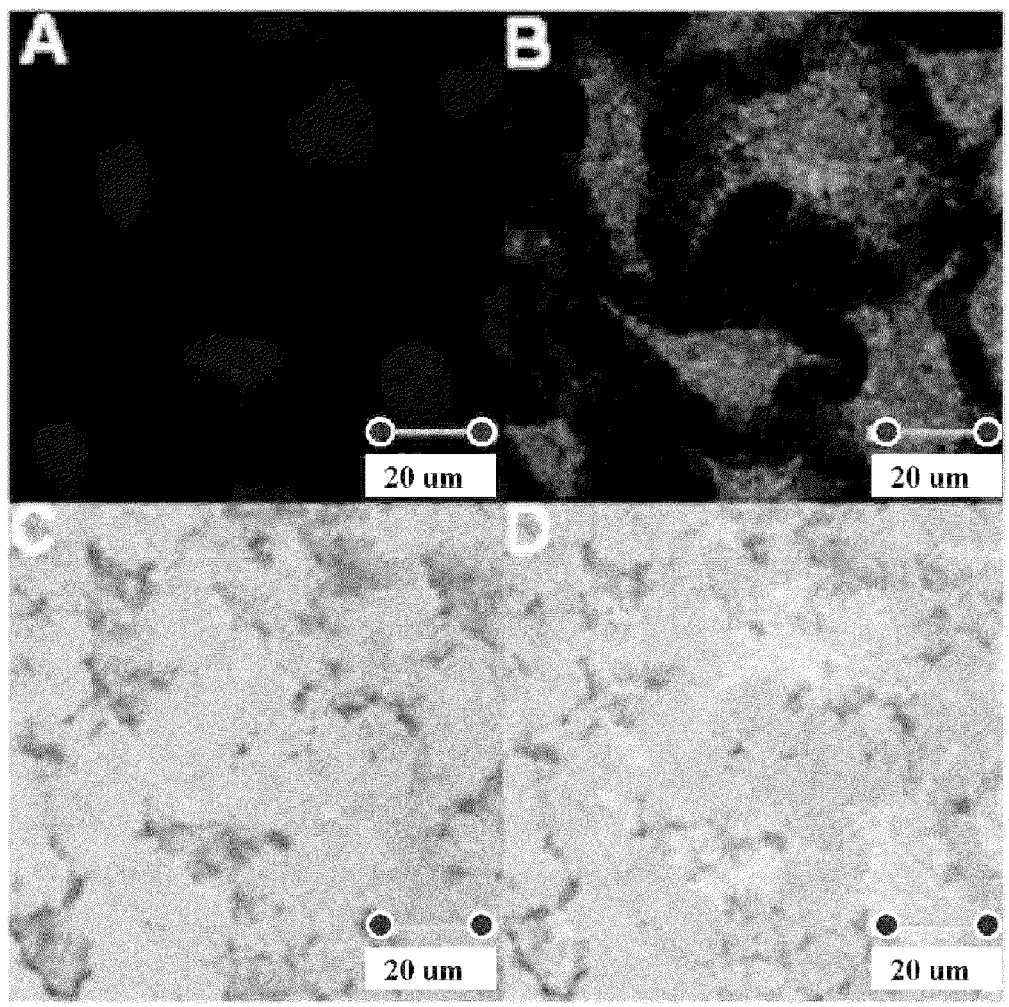
FIG. 2 shows representative confocal fluorescence microscopy images of HeLa cells. A) The cell nuclei were stained using DAPI. B) HeLa cells were exposed to 1.0 nM AuNP GDS-Mcl1-1L-AS-FITC conjugates. C) Transmission image of HeLa cells. D) Overlay image of images A, B, and C.

Fluorescence microscopic analyses showed the presence of fluorescence from the Mcl1-1L-AS-FITC in every cell tested (FIG. 2), indicating an excellent transfection efficiency of the AuNP GDS-Mcl1-1L-AS-FITC. It has been known that single-stranded DNA functionalized gold nanoparticles readily enter cells. Our results show that the AuNP GDS-AS conjugates containing a partially double-stranded (20 base-pairs) DNA also enter cells with nearly 100% efficiency. AuNP GDS-AS conjugates were mixed with the antisense oligonucleotide (0.1 or 1 µM) in annealing buffer (1× phosphate-buffer saline containing 0.3 M NaCl) by gently shaking for 10 min, incubated at 55° C. for 10 min, and cooled downed to room temperature for about 1 hr. The resulting conjugates were washed with phosphate buffer saline (PBS, pH 7.4) three times before applying the conjugate to cells.

Example 2

Verification for Knockdown of Target Gene Expression

Figure 3:
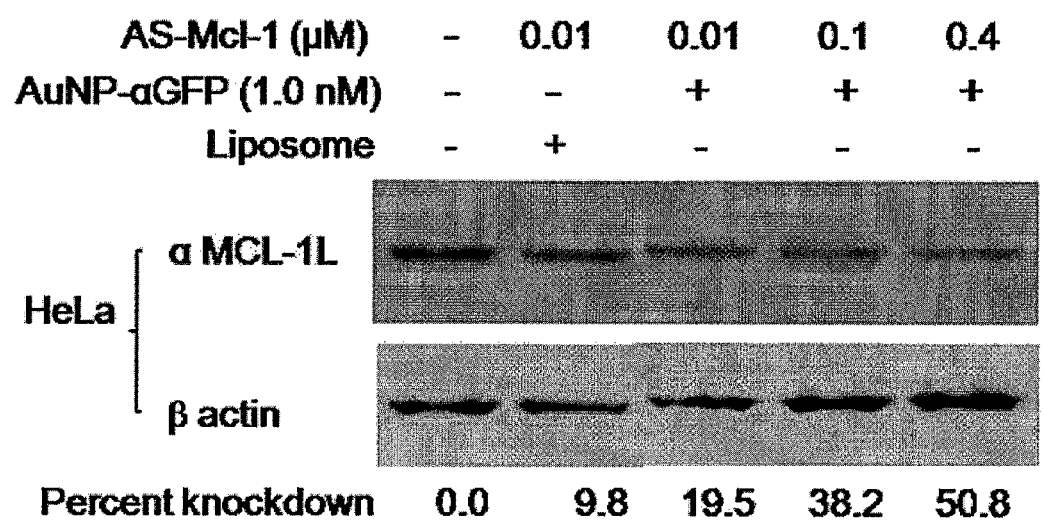
FIG. 3 represents dose response of each Au NP-GDS-antisense oligo complex to gene knockdown in HeLa cells. Percent knockdown indicates the percentage of knockdown.

Next, we tested the ability of the antisense oligo to knockdown the target gene expression. The AuNP GDS-Mcl-1L-AS conjugates were applied to the HeLa cells, protein samples were prepared from the cultures 24 hrs after transfection for quantitative analysis of MCL-1L using western blot analyses. As shown in FIG. 3, AuNP GDS-Mcl-1L-AS conjugates efficiently knockdowned the MCL-1L expression in a manner dependent on MCL-1L antisense concentrations. When 0.1 µM Mcl-1L AS was delivered into the cells using a liposome-based reagent (Lipofectamine 2000, Invitrogen), the knockdown efficiency was lower than AuNP GDS (9.8% vs. 19.5%), indicating that the AuNP GDS system is more efficient in delivering antisense DNA than the liposome-based reagent.

Example 3

AuNP GDS as Gene Delivery System

To investigate the ability of AuNP GDS as a general gene delivery system, we further tested another human cell line (HEK 293T, human embryonic kidney 293T; Korean Cell Line Bank) as well as two additional antisense DNAs which targeted a gene.

Figure 7A:
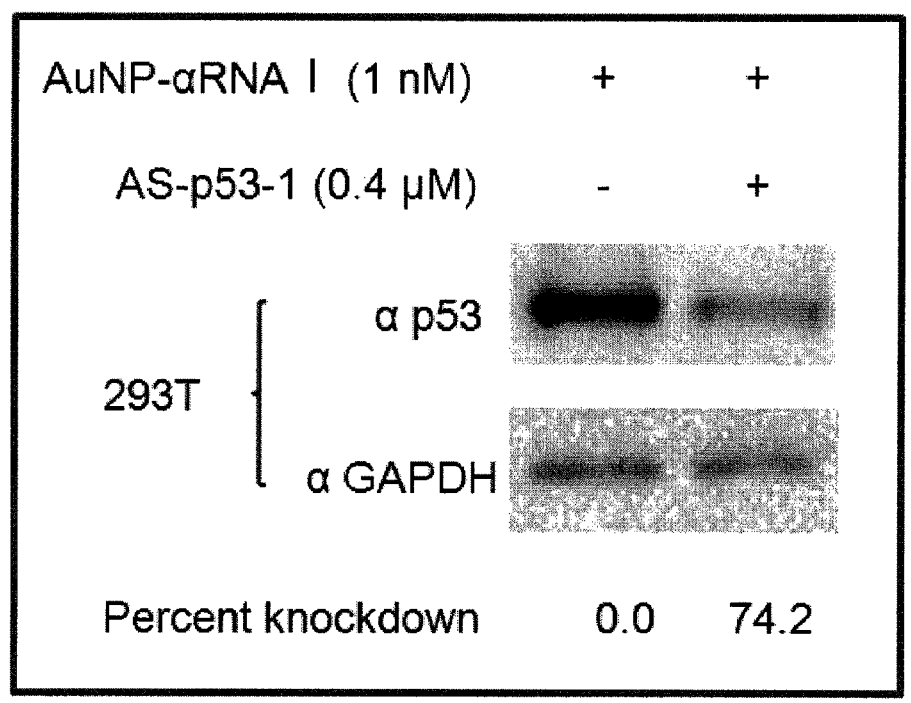
FIG. 7a is a result to knockdown p53 expression by antisense oligo delivered using AuNP-αRNA I.

293T ($4.5 \times 10^5$) or HeLa cells ($3.0 \times 10^5$) were incubated with antisense oligo functionalized with gold-nanoparticle in 6-well dishes. Cell lysates were prepared in NP-40 lysis buffer (50 mM Tris-HCl, pH 8.0, 0.15 M NaCl, and 1% NP-40) containing 10% protease inhibitor cocktail (Sigma). For quantitative protein analysis, a standard curve was established with the standard BSA solution (Pierce, Rockford, Ill., USA), and cell lysates containing equal amount of total protein were subjected to sodium dodecyl sulfate-polyacrylamide gel electrophoresis (SDS-PAGE). Separated proteins were transferred onto nitrocellulose membrane and Western blot analyses were performed. Anti-MCL-1L and anti-p53 monoclonal antibodies (Santa Cruz Biotechnology, Santa Cruz, Calif., USA) were used to detect MCL-1L and p53, respectively.

p53 is a well characterized transcription factor which plays a crucial role in the maintenance of cell-cycle arrest after DNA damage and in apoptosis as a tumor suppressor.[12] Antisense DNAs to the p53 gene contained a sequence complementary to AuNP GDS followed by a 20 nucleotide-sequence complementary to either an internal coding region of Mcl-1L (bases 886 to 905; 5'-CCCTGCTCCCCCCTGGCTCC-3' (SEQ ID NO:4)) for AS-Mcl-1L,[13] or to the region covering the six base pairs immediately before the first codon and the first four coding codons of p53 for AS-p53-2 (5'-GGGCAC-CACCACACTATGTCGAA-3'(SEQ ID NO:5)) [14]. The conjugates were incubated with HeLa cells or 293T cells. After 24 hrs incubation, the cells were harvested and the expressions of target proteins were quantified using GAPDH (Glyceraldehyde 3-phosphate dehydrogenase) as a reference protein. The results showed that the three nanoconjugates efficiently decreased the levels of target proteins in two different human cell lines (FIG. 4). In addition, AuNP GDS itself did not affect expression levels of target proteins and a reference protein. These data demonstrate that AuNP GDS can be used as a general gene delivery system for antisense DNAs specific to any gene of interest in different human cell lines. We also tested another AuNP GDS containing an oligo sequence bearing a partial sequence of RNA I (bases 13 to 30), which is involved in the replication of ColE1-type plasmid in *Escherichia coli*[9]. The antisense DNA (AS-p53-1) containing nucleic acids complementary to the sequence of RNA I oligo used was conjugated with AuNP GDS, and the resulting conjugates were applied to HeLa or 293T cells. The similar results were obtained as described in FIG. 4 (FIG. 7).

Example 4

Stability of DNA Oligonucleotide on Gold Nanoparticle

It is well known that single or double stranded DNA oligonucleotides on gold nanoparticle show greatly enhanced stability relative to DNA or RNA oligonucleotides themselves in the cell [15]. This stability may be due to steric hindrance and high local concentration of salts, which can deactivate enzymatic activity of nucleases. To be effective antisense nucleic acids, their activity needs to be stably maintained in a prolonged incubation time in the cell.

Figure 5A:
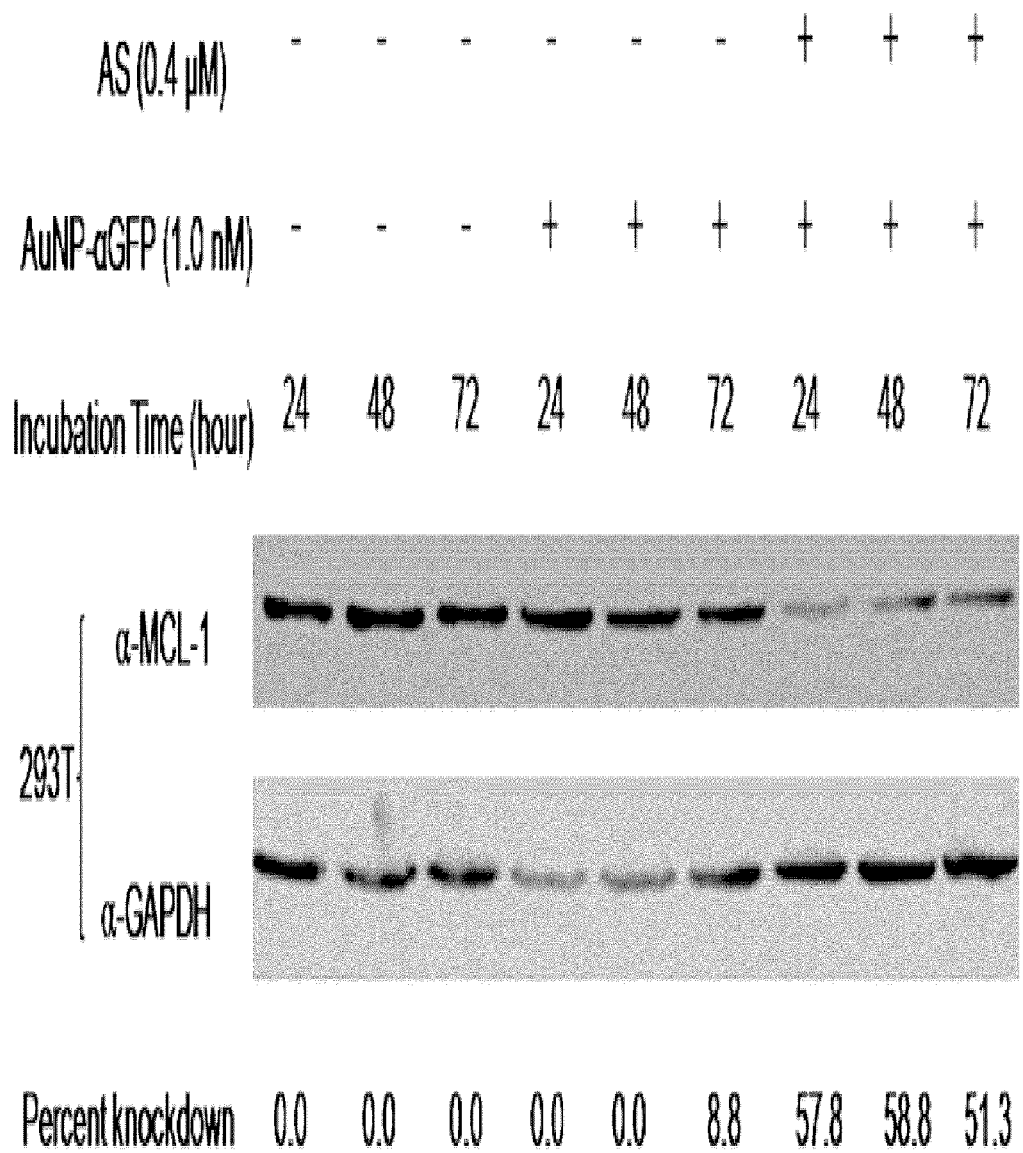
FIG. 5 shows knockdown efficiency of α-McL-1 expression by Au NP-GDS-AS-Mcl-1 conjugates in HeLa Cells as incubation time.
Figure 5B:
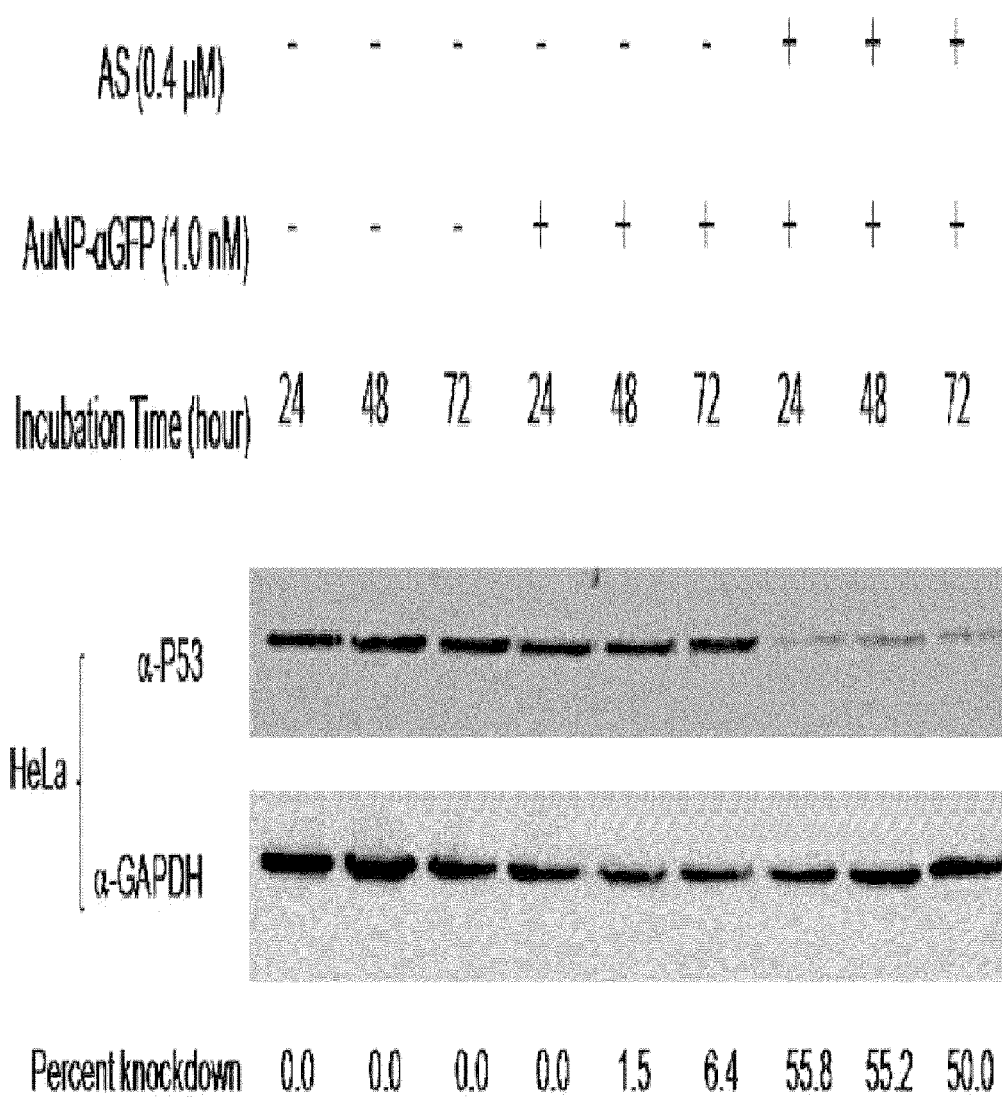

For this reason, we examined the incubation time-dependent efficiency of AuNP GDS-AS by measuring the degree of knockdown levels of target protein expression in HeLa cells for three days. The knockdown efficiency was decreased slightly from 57.8 to 51.3% for MCL-1L in 293T cells while it was decreased from 55.8 to 50.0% for p53 in HeLa cells after three day incubation (FIG. 5). These results show that approximately 90% of the activity of antisense DNAs delivered by AuNP GDS was maintained for three days in human cells.

Example 5

Determination of the Number of AS DNA on the AuNP GDS

Figure 6A:
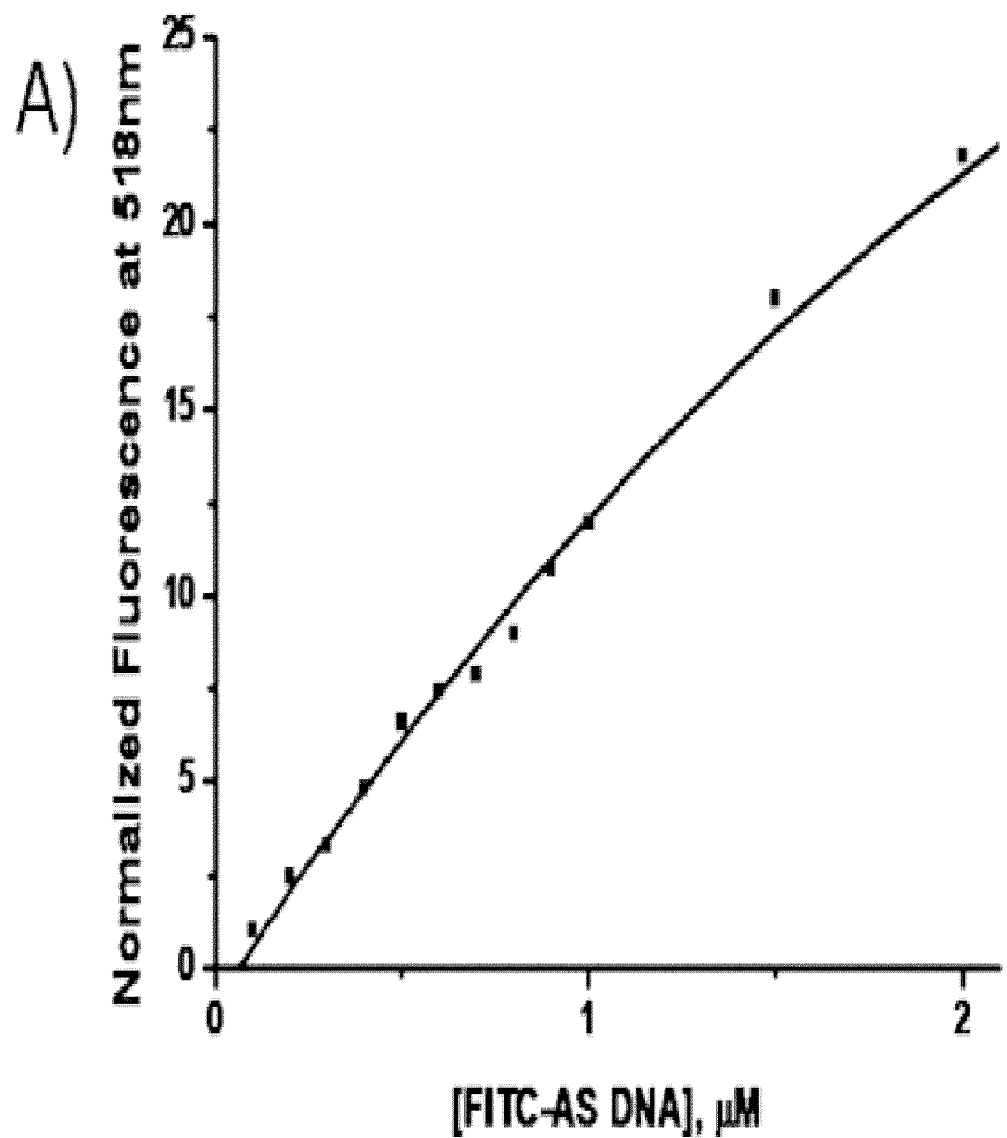
FIG. 6 is a result determining the number of AS DNA on one AuNP GDS. A) a graph for calibrations cure of FITC-antisense oligonucleotide. Each vertical and horizontal axis indicates fluorescence at 518 nm and concentration of FITC-antisense DNA. B) Number of AS DNA on one AuNP GDS. The vertical axis means the number of FITC-DNA on AuNP in the preparation of AuNP-FITC-antisense DNA complex. The horizontal axis indicates the concentration of FITC-DNA mixed with 10 nM AuNP in the preparation of AuNP-FITC-antisense DNA complex.
Figure 6B:
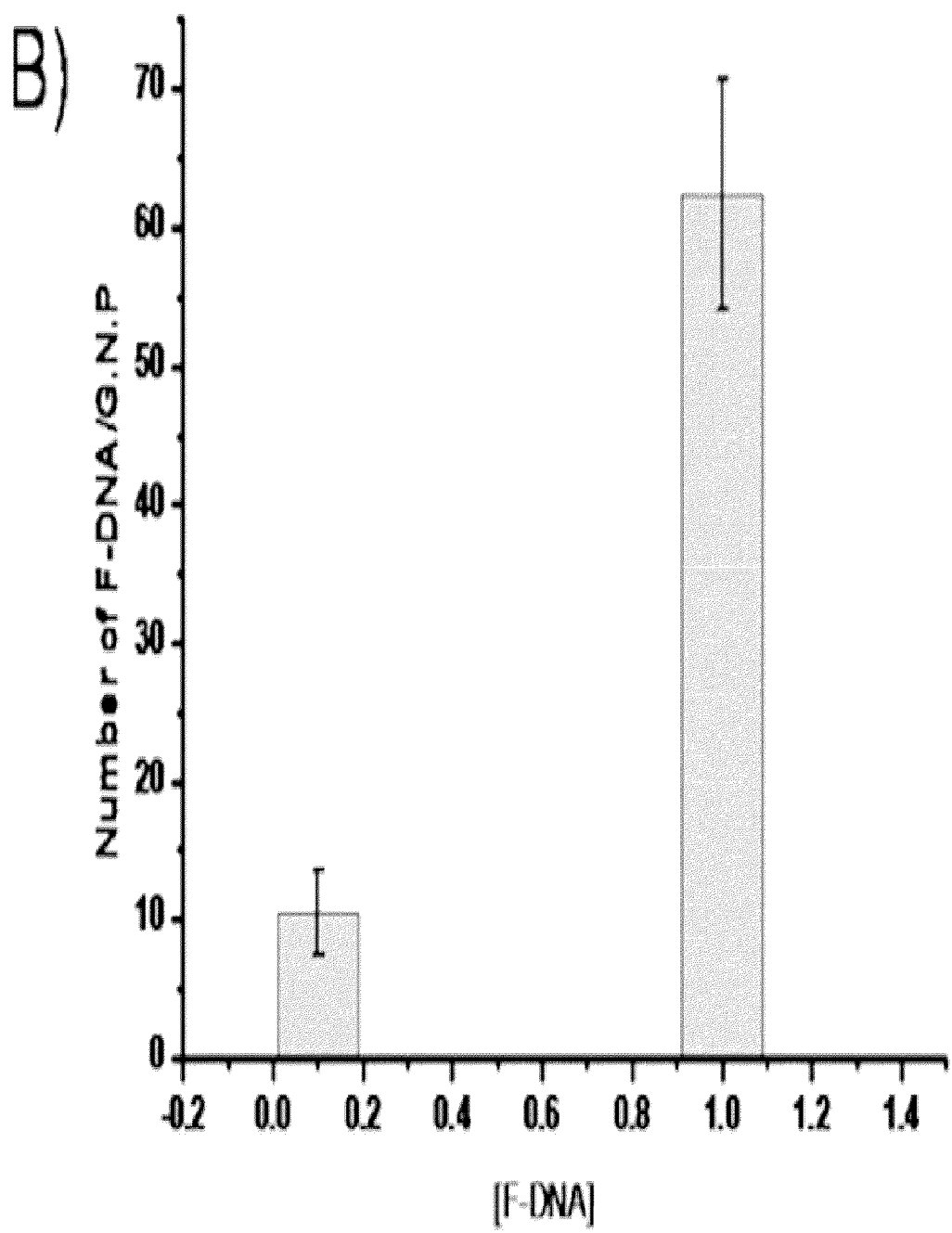

AuNP GDS was mixed with the FITC-antisense oligonucleotide (0.1 or 1 μM) in annealing buffer (1× phosphate-buffer saline containing 0.3 M NaCl) by gently shaking for 10 min, incubated at 55° C. for 10 min, and cooled downed to room temperature for 1 hr. The resulting conjugates were centrifuged at 10,000×g for 20 min at 4° C. The loadings of FITC-antisense oligonucleotide on the AuNP GDS were estimated from fluorescence measurements of the supernatant after the coupling reaction using the calibrations cure of FITC-antisense oligonucleotide (FIG. 6).

Example 6

Cell Viabilities in the Presence with Various Concentration of Au GDS

HeLa cells were transfected with 0, 1, 5 or 10 nM gold nanoparticle-anti GFP, and incubated for 48 hrs. Viable cells were counted after staining dead cells with trypan blue.

In conclusion, we proved single strand DNA functionalized gold nanoparticle (AuNP GDS) can be used as a gene delivery system for oligo antisense DNAs specific to any gene of interest without affecting normal cell physiology. Compared to other commonly used gene delivery systems based on liposome formation or RNA based knockdown systems that facilitate degradation of target mRNA by the use of RNA-induced silencing complex (RISC), which normally participates in the regulation of hundreds of mRNA stability to maintain normal cellular processes[17], oligo antisense DNAs delivered by the AuNP GDS system do not require or sequester normal cellular machinery for the knockdown of target gene expression, which is assumed to be mediated by inhibition of translation by formation of mRNA-antisense DNA dupex. Thus, oligo antisense DNAs delivered by the AuNP GDS system only knockdown the target gene expression without interfering with normal cellular processes. Not only the AuNP GDS-antisense conjugates efficiently knockdowned the expression of target proteins, but also the system was more efficient than the commercially available gene transfer reagent (Lipofectamine 2000) in respect to the degree of knockdown of target protein expression. Moreover, the activity of antisense DNAs delivered by the AuNP GDS lasted for three days. Taken together, our results demonstrate that the AuNP GDS is an excellent gene delivery system. This system may be also easily applicable to the delivery of siRNA, ribozyme, and PNA (peptide nucleotide acid).

Example 7

Transfer of shRNA on AuNP and Inhibition of Target Gene Expression

Figure 8A:
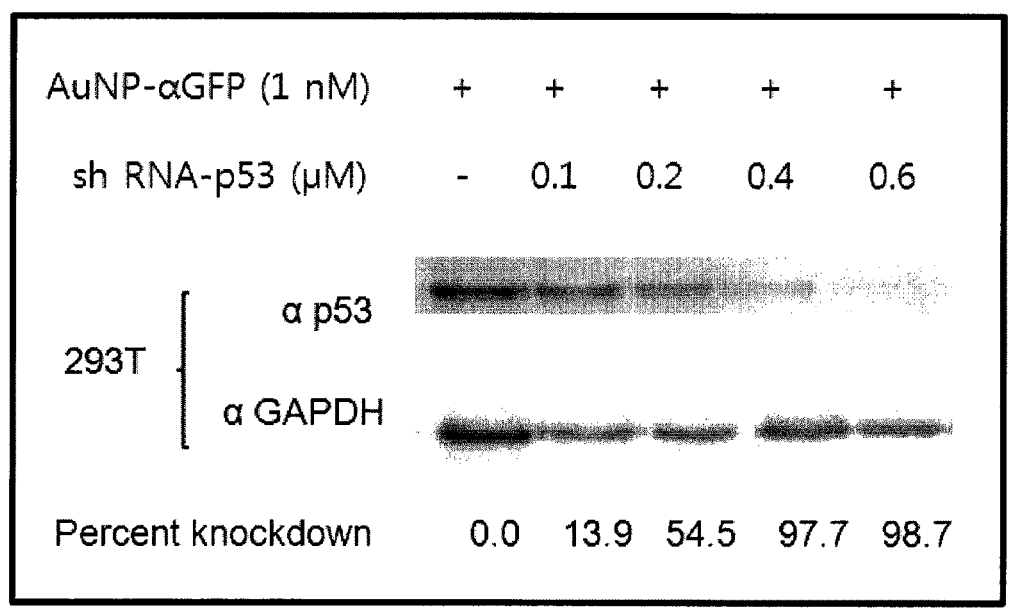
FIG. 8a is a result to knockdown p53 expression by shRNA delivered using AuNP-αGFP.
Figure 8C:
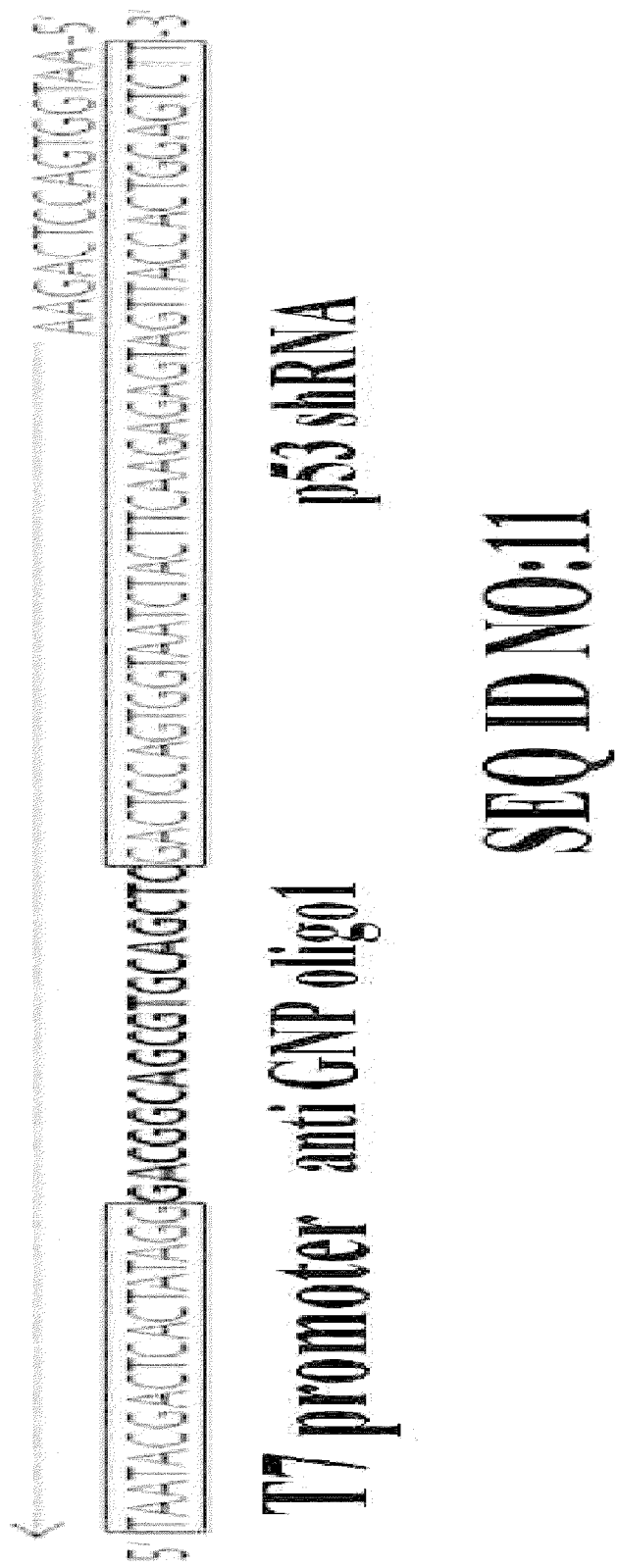

The shRNA was tested for knockdown of target gene expression. siRNA is an efficient gene knockdown tool to suppress target gene expression. The sh-p53-1[18] contained a sequence complementary to AuNP GDS followed by a nucleotide-sequence complementary to the p53 coding region (5'-GACUCCAGUGGUAAUCUACUUCAA-GAGAGUAGAUUACCACUGGAGUCUU-3'SEQ ID NO:6)). The synthetic procedure for the shRNA to the p53 was described in FIG. 8C. Using the MEGAshortscript™ kit (Ambion, THE RNA COMPANY) according to the manufacturer's instruction, sh-p53 was synthesized from PCR DNAs containing the sequence of T7 promoter followed by anti-EGFP oligo and the sequence complementary to the p53, which form a loop structure. AuNP GDS-sh-p53-1 conjugates were prepared by the same method of antisense oligo, and applied to 293T cells. To quantitate p53 using Western blot analysis, protein samples were harvested after transfection and incubation for 24 hrs. As shown in FIG. 8a, AuNP GDS-sh-p53 conjugates effectively knockdowned the expression of p53 in a manner dependent on the concentration of sh-p53 antisense bound to them.

Example 8

Verification of Gene Delivery on Gold Nanoparticle

Figure 9B:
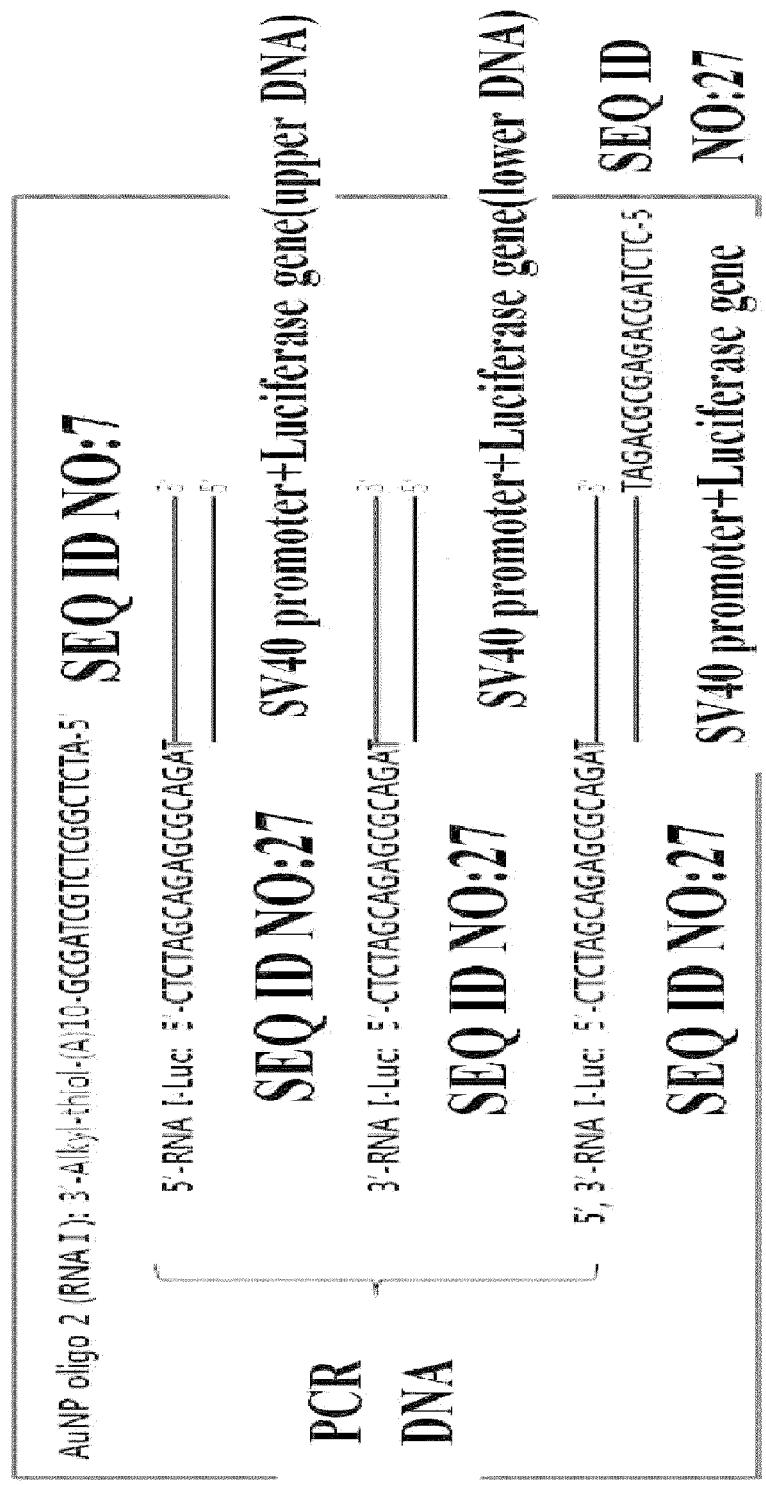
FIG. 9b represents nucleotide sequences and schematic diagram including SV40 promoter and luciferase gene synthesized using an oligonucleotide of AuNP-αRNA I (SEQ ID NO:7) covalently linked to the surface of the nanomaterial as the universal binding partner, the complementary oligonucleotide thereof (SEQ ID NO: 27) as the binding counter-partner having the sequence complementary to the binding partner, and PCR.
Figure 9D:
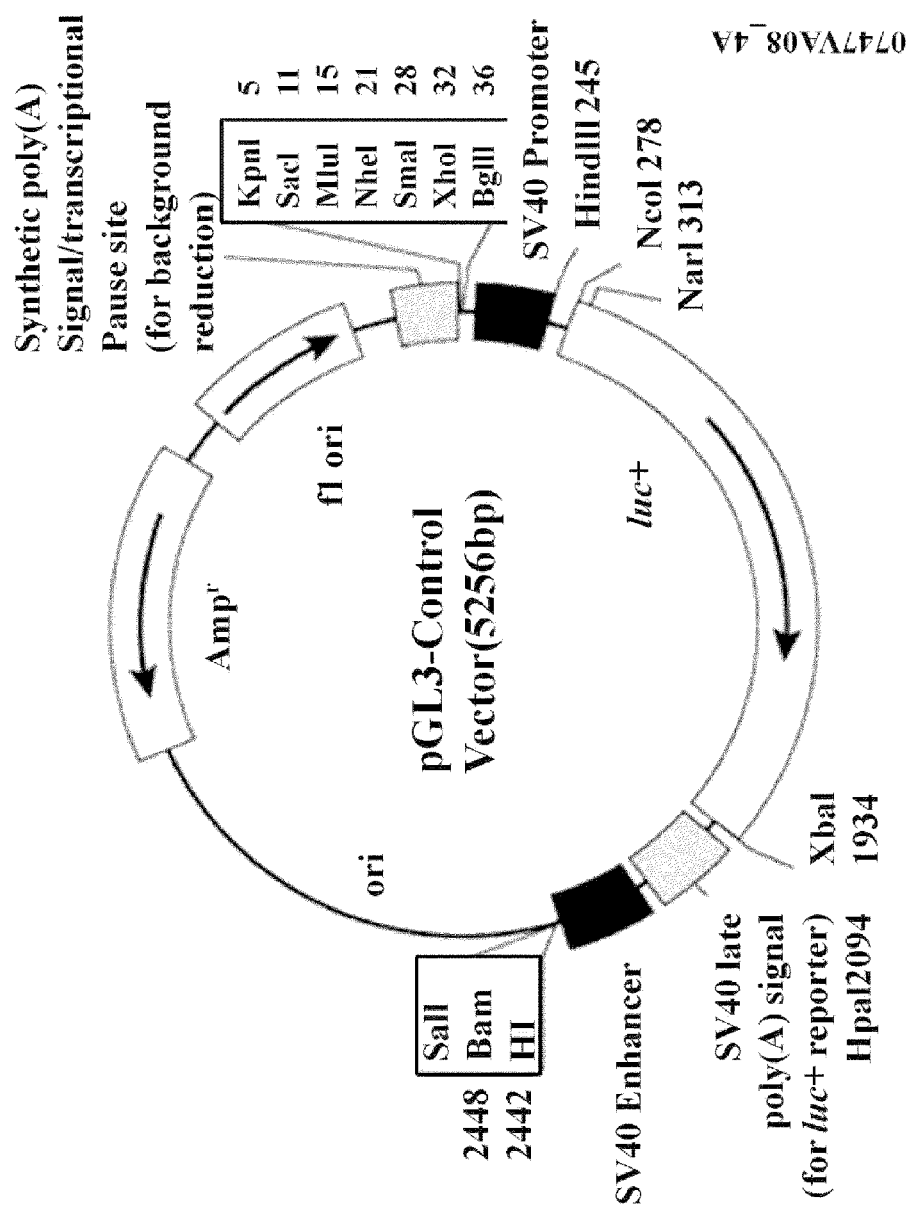
FIG. 9d schematically represents a map of pGL3-Control plasmid.

It was tested whether double strand DNA containing anti-RNA I sequence using AuNP GDS is delivered into cells. To measure the activity of gene delivered into cells, the luciferase gene as a fluorescence enzyme was used. As shown in FIG. 9, to prepare PCR DNA containing luciferase gene (bases 2431 to 2450) and SV40 promoter as pGL3 control plasmid, polymerase chain reaction (PCR) was carried out using a primer with the complementary sequence thereof and another primer containing SV40 promoter and anti-RNA I sequence having Origin capable of being replicated in the 293T cells. To construct single strand DNA containing anti-RNA I sequence at both 5'- and 3'-end of the resulting PCR DNA, C6 linker was involved in the next to αRNA I sequence placed at 5'-end of primers, respectively. AuNP-GDS was conjugated with three products (5',3'-αRNA I-Luc., 5'-αRNA I-Luc., 3'-αRNA I-Luc) obtained from PCR reaction. For complementary binding of AuNP in an easy manner, each PCR products was denatured at 95° C. for 5 min and then mixed with AuNP GDS in annealing buffer (1× phosphate-buffer saline containing 0.3 M NaCl) at 55° C. for 10 min, and cooled downed to room temperature for about 1 hr. The following procedure is performed according to the preparation method of AuNP GDS. The synthetic AuPN GDS-Luc (luciferase gene) was applied to 293T cells. After expression of luciferase gene in the cells, cells were collected and luciferase activity was measured (Luciferase Assay Kit, PROMEGA). Luciferase fluorescence enzyme releases fluorescence by redox reaction with Luciferin. As described in FIG. 9a, the products having αRNA I nucleotide sequence at 5'-end (5'-αRNA I-Luc.) had luciferase activities, suggesting a feasible delivery of double strand DNA gene into the cells by AuNP-GDS.

Example 9

Construction of Single-Stranded DNA Functionalized Gold Nanoparticles

Single-stranded DNA functionalized gold nanoparticles (AuNP) developed by Rosi et al. [8] showed efficient delivery of antisense DNA into human cells and, consequently knockdown of target gene expression. These functionalized gold nanoparticles also exhibited lower cellular toxicity than antisense DNA delivered by liposome-based reagents. To circumvent the inconvenience of the system that can deliver antisense DNA covalently cross-linked to gold nanoparticles, which needs to be individually synthesized for each gene of interest, we tested whether single-stranded DNA functionalized AuNP can be used as a universal carrier for the delivery of small hairpin RNA (shRNA) specific to any gene of interest. We used a DNA oligonucleotide (oligo) bearing a sequence complementary to the coding region (bases 1198 to 1215) of EGFP (an αEGFP oligo), which has been shown to be effective in the delivery and silencing of EGFP expression in human tissue cultures without interfering with expression of any other genes [8]. AuNP•αEGFP oligo complex was prepared by functionalizing 13 nm gold nanoparticles with thiolated αEGFP oligos [10].

Example 10

Effects of Delivery of shRNAs by AuNP•αEGFP Oligo Complex

Figure 10:
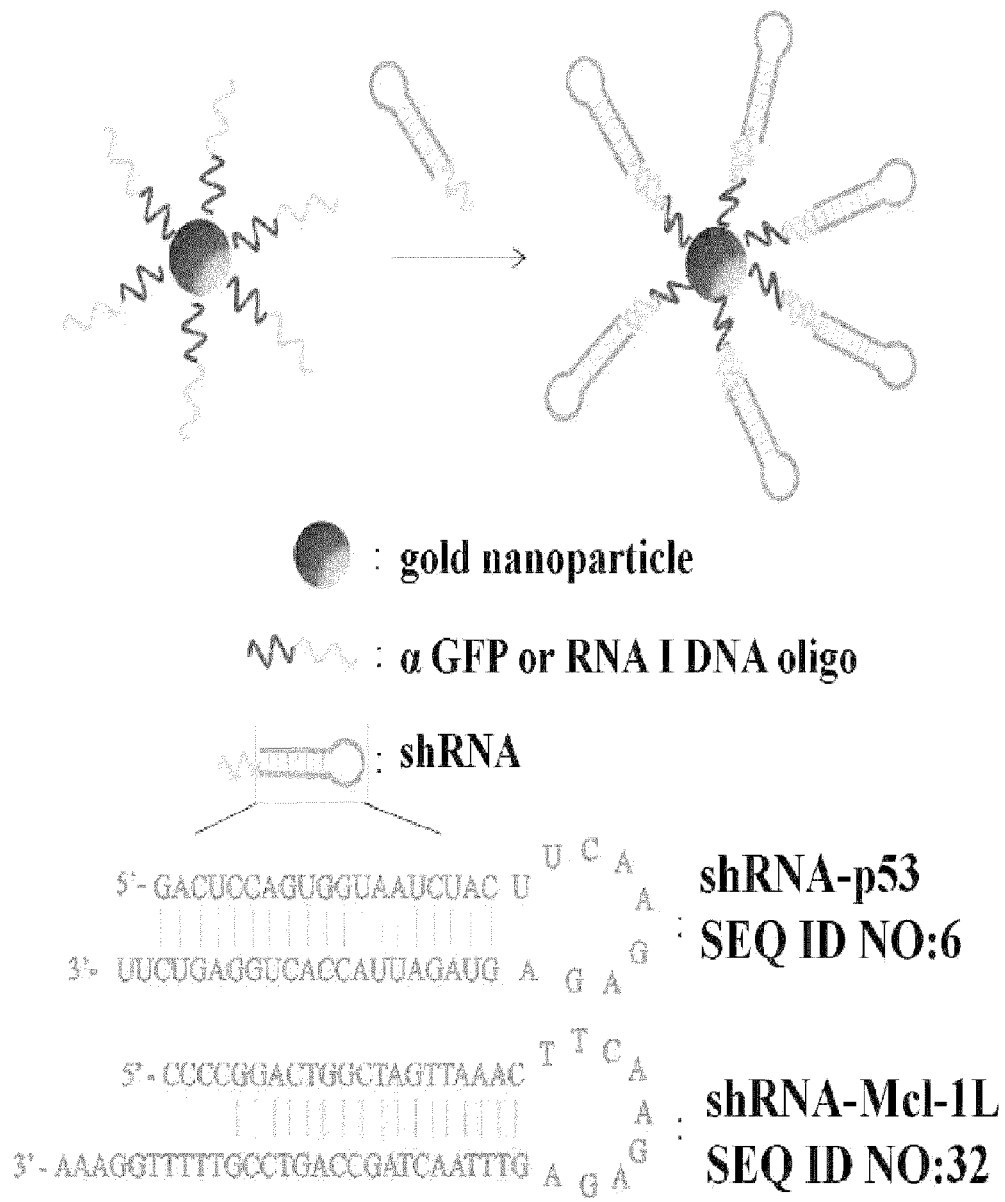
FIG. 10 schematically represents single-stranded DNA functionalized gold nanoparticle and shRNA conjugates. Sequences of shRNAs used in this study are (SEQ ID NO6and SEQ ID NO:32).
Figure 11A:
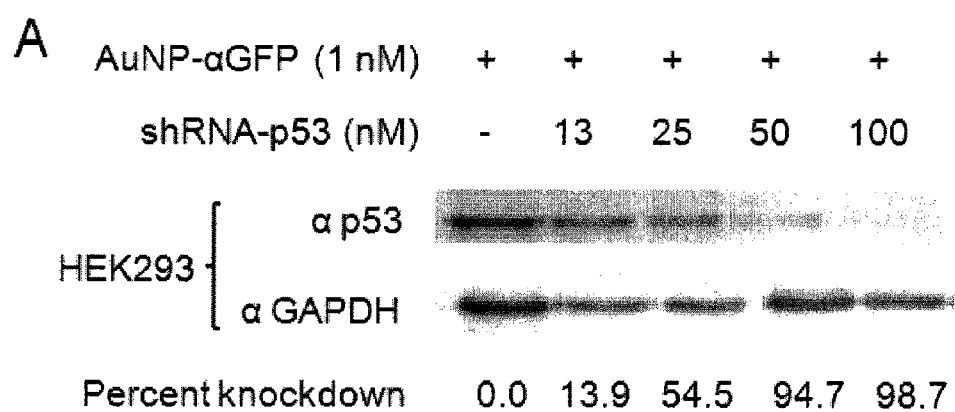
FIG. 11 represents effects of shRNAs delivered by single-stranded DNA functionalized gold nanoparticles. A. Dose response of AuNP•αEGFP•shRNA-p53 conjugates to p53 gene knockdown in HEK293 cells. HEK293 cells were incubated with AuNP•αEGFP•shRNA-p53 conjugates and harvested 24 hr after treatment for western blot analysis. B. Knockdown efficiency of shRNA-p53 delivered by AuNP•αEGFP in HEK293 and HeLa cells. Cells were treated with either AuNP•αEGFP•shRNA-p53 conjugates or a mixture of shRNA-p53 and lipofectamine and harvested 24 hr after treatment for western blot analysis. C. Duration of knockdown effects on p53 gene expression by AuNP•αEGFP•shRNA-p53 conjugates. HeLa cells were treated with AuNP•αEGFP•shRNA-p53 conjugates and harvested at time intervals indicated for western blot analysis. D. Knockdown of Mcl-1L expression by AuNP•αEGFP•shRNA-Mcl-1L in HeLa cells. HeLa cells were treated with AuNP•αEGFP•shRNA-Mcl-1L conjugates and harvested 24 hr after treatment for western blot analysis. E. Effects of AuNP•αEGFP•shRNA-p53 conjugates on the steady state levels of p53 mRNA in HeLa cells. HeLa cells were treated with AuNP•αEGFP•shRNA-p53 conjugates and harvested 24 hr after treatment for total RNA isolation. The isolated RNA was used for semi-quantitative RT-PCR.
Figure 11B:
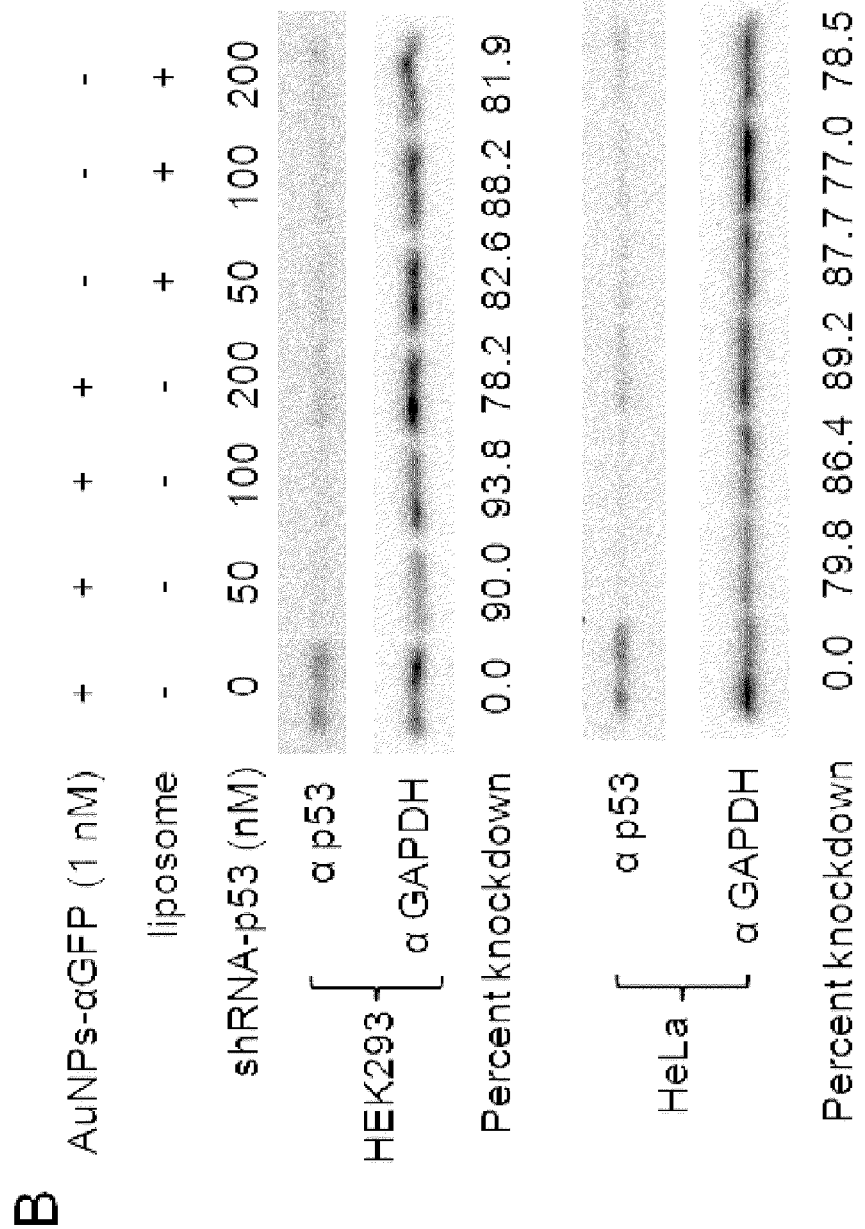

Next, shRNA specific to the p53 gene was synthesized in vitro and annealed to αEGFP oligos that were covalently cross-linked to AuNP, and the resulting conjugates were applied to HEK293 cells. The shRNA to the p53 gene (shRNA-p53) contained a sequence complementary to αEGFP oligo followed by a 67 nucleotide-sequence that forms a hairpin (FIG. 10). The hairpin functions as short interfering RNA and contains inverted direct repeats corresponding to an internal coding region of p53 (bases 895 to 913) flanked by a loop composed of 9 nucleotides [16]. AuNP•αEGFP•shRNA-p53 conjugates were applied to HEK293 cells and protein samples were prepared from the cultures 24 hours after transfection for quantitative analysis of p53 using western blot analysis. As shown in FIG. 11A, AuNP•αEGFP•shRNA-p53 conjugates efficiently knocked down p53 expression in an shRNA-p53 concentration dependent manner. Application of shRNA-p53 at concentrations above 50 nM repressed over 90% of p53 expression. When shRNA-p53 was delivered into cells using a liposome-based reagent, the knockdown efficiency was similar to that of AuNP•αEGFP (FIG. 11B). We tested another human cell line, HeLa for transfection of shRNA-p53 annealed to AuNP•αEGFP and obtained results analogous to those from HEK293 cells (FIG. 11B), indicating that AuNP•αEGFP-mediated delivery of shRNA is not specific to cell lines.

Figure 11C:
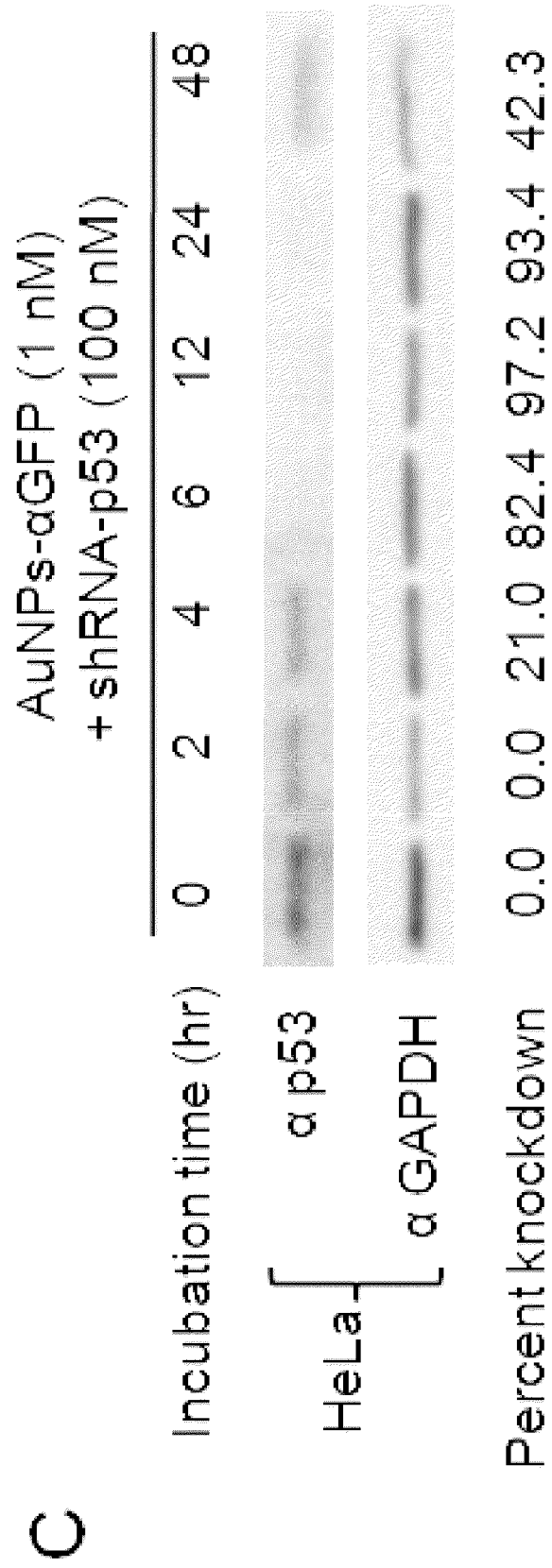

To be effective as an shRNA, the activity needs to be stably maintained for a prolonged incubation time in the cell. For this reason, we examined the incubation time-dependent efficiency of AuNP•αEGFP•shRNA-p53 by measuring the degree of knockdown levels of p53 protein expression in HeLa cells at various time intervals. The knockdown efficiency was increased slightly from 0 to 21.0% from 4 to 6 hr incubation and dramatically to over 97% during 12 to 24 hr incubation (FIG. 11C). It was decreased to 35.3% ater 48 hr incubation. These results show that most of the activity of shRNA delivered by AuNP•αEGFP was maintained at least for 24 hr in human cells.

Figure 11D:
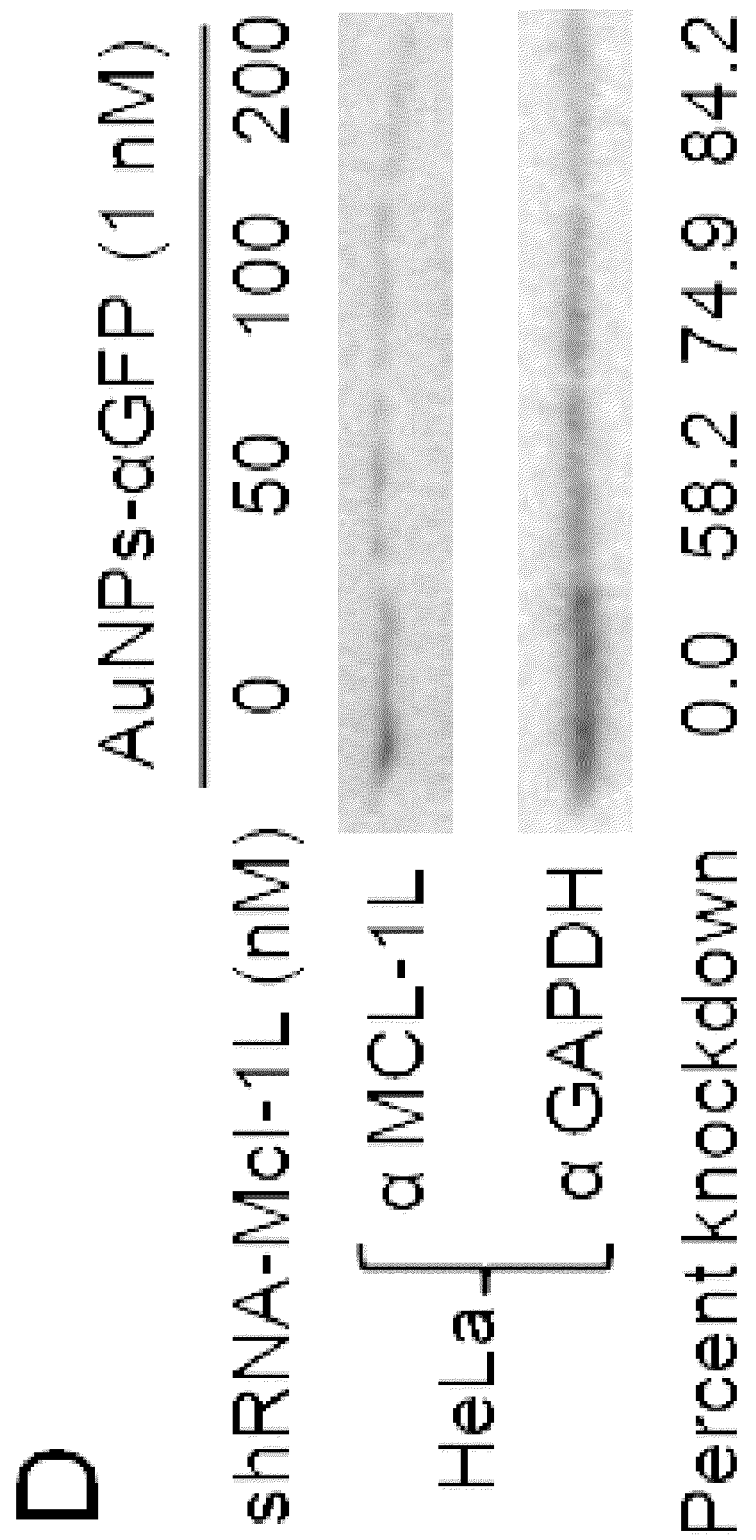

To investigate the ability of AuNP•αEGFP as a general gene delivery system, we tested an additional shRNA that targeted Mcl-1L (myeloid cell leukemia-1 long) gene, which encodes an anti-apoptotic Bcl-2 family protein. The shRNA to the Mcl-1L gene (shRNA-Mcl-10 contained a sequence complementary to αEGFP oligo followed by a 78 nucleotide-sequence that forms a hairpin (FIG. 10). The hairpin contained inverted direct repeats corresponding to an internal coding region of Mcl-1L (bases 906 to 925) flanked by a loop composed of 9 nucleotides [17]. The AuNP•αEGFP•shRNA-Mcl-1L conjugates were incubated with HeLa cells. After a 24-hour incubation, cells were harvested and the expressions of target proteins were quantified using western blot analysis. The nanoconjugates efficiently decreased the levels of MCL-1L protein in HeLa cells (FIG. 11D).

Figure 11E:
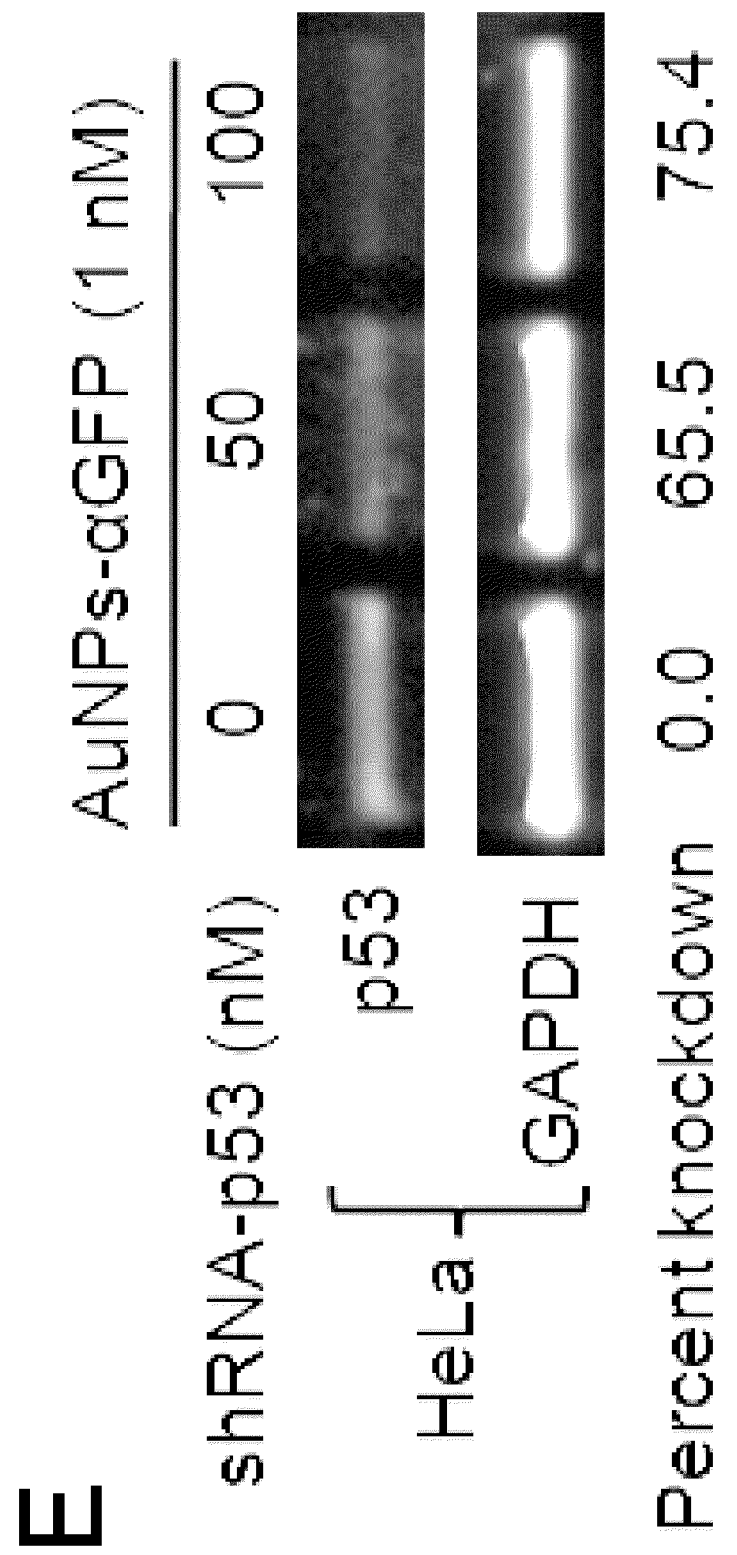

Next, we measured steady-state levels of p53 mRNA in HeLa cells treated with AuNP•αEGFP•shRNA-p53. They were decreased to a less than 35% those of untreated cells as measured using semi-quantitative RT-PCR (FIG. 11E). Based on these results, we conclude that AuNP•αEGFP mediated knockdown of gene expression resulted from a rapid degradation of target mRNA.

Example 11

Figure 12:
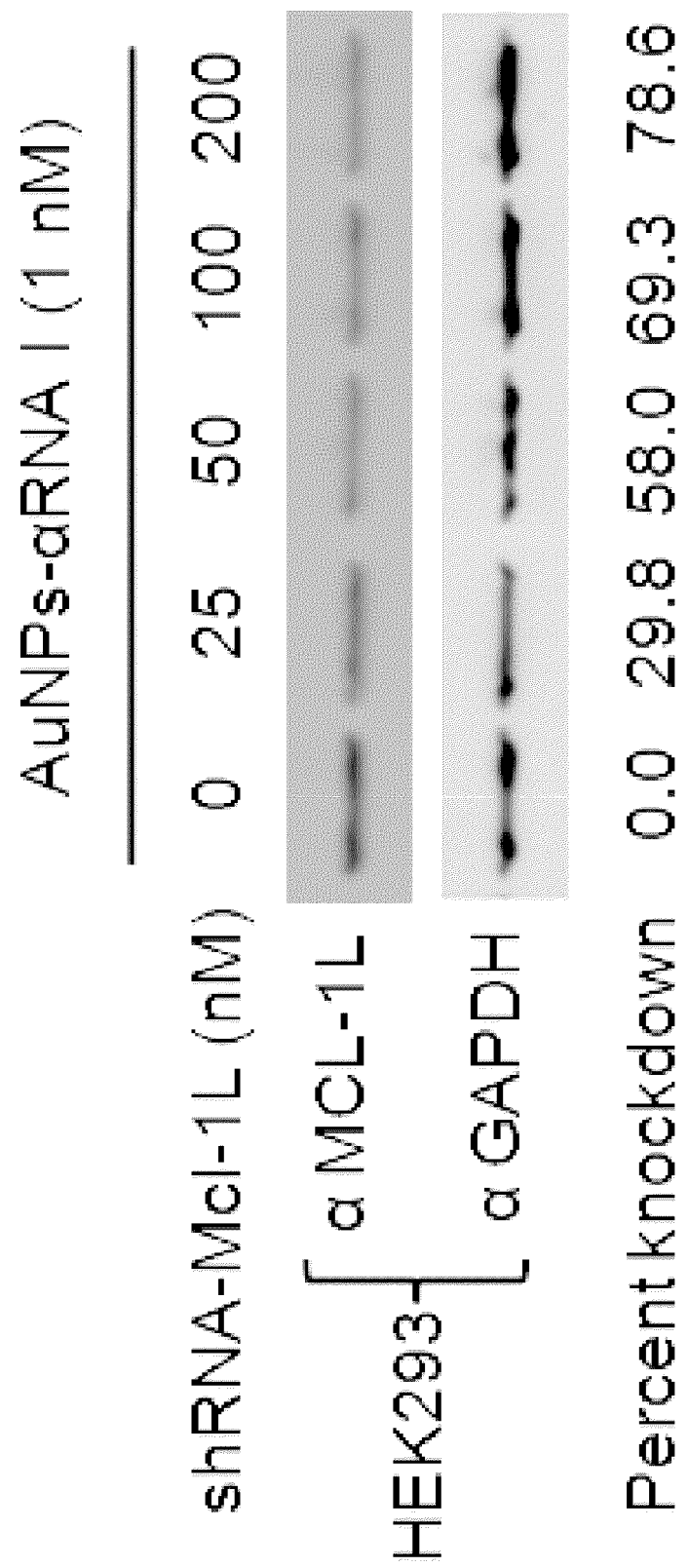
FIG. 12 represents knockdown of Mcl-1L expression by AuNP•RNA I•shRNA-Mcl-1L in HEK293 cells. HEK293 cells were treated with AuNP•RNA I•shRNA-Mcl-1L conjugates and harvested 24 hr after treatment for western blot analysis.

Effects of the Sequence of DNA Oligo on Efficiency of shRNA Delivery by Single-Stranded DNA Functionalized AuNP We also tested another single-stranded DNA functionalized AuNP that contained an oligonucleotide (oligo) bearing a partial sequence of RNA I (AuNP•RNA I), which is an antisense RNA for the replication of ColE1-type plasmid in *Escherichia coli* [18]. An shRNA similar to the shRNA-Mcl-1L that was used for the experiment described in FIG. 11E except having a sequence complementary to the sequence of RNA I oligo was annealed to AuNP•RNA I and the resulting conjugate was incubated with HEK293 cells. Analogous results to those shown in FIG. 11E were obtained (FIG. 12).

In conclusion, we have shown that single-stranded DNA functionalized gold nanoparticles can be used as gene delivery systems for shRNAs specific to any gene of interest. Not only did the AuNP•αEGFP-shRNA conjugates efficiently knock down the expression of target proteins, but the system was also as efficient as commercially available gene transfer reagents in respect to the degree of knockdown of target protein expression. Taken together, our results demonstrate that the single-stranded DNA functionalized gold nanoparticles are an excellent gene delivery system for shRNA.

Having described a preferred embodiment of the present invention, it is to be understood that variants and modifications thereof falling within the spirit of the invention may become apparent to those skilled in this art, and the scope of this invention is to be determined by appended claims and their equivalents.

References

[19] a) F. McCormick, *Nat. Rev. Cancer* 2001, 1, 130-141; b) J. B. Opalinska, A. M. Gewirtz, *Nat. Rev. Drug Discov.* 2002, 1, 503-514.

[29] M. A. Kay, J. C. Glorioso, L. Naldini, *Nat. Med.* 2001, 7, 33-40.

[39] a) S. E. Raper, N. Chirmule, F. S. Lee, N. A. Wivel, A. Bagg, G.-R Gao, J. M. Wilson, M. L. Batshaw, *Mol. Genet. Metab.* 2003, 80, 148-158; b) S. Hacein-Bey-Abina, C. von Kalle, M. Schmidt, F. Le Deist, N. Wulffraat, E. McIntyre, I. Radford, J. L. Villeval, C. C. Fraser, M. Cavazzana-Calvo, et. al, *N. Engl. J. Med.* 2003, 348, 255-256; c) J. J. Green, R. Langer, D. G. Anderson, *Acc. Chem. Res.,* 2008, 41, 749-759.

[49] I. M. Verma, N. Somia, *Nature* 1997, 389, 239-242.

[59] a) M. A. Mintzer, E. E. Simanek, *Chem. Rev.* 2009, 109, 259-302; b) X. Guo, F. C. Szoka Jr., *Acc. Chem. Res.,* 2003, 36, 335-341; c) R. K. Tekade, P. V. Kumar, N. K. Jain, *Chem, Rev.,* 2009, 109, 49-87; d) K. S. Soppimath, T. M. Aminabhavi, A. R. Kulkarni, W. E. Rudzinski, *J. Control. Release,* 2001, 70, 1-20.

[69] a) M. Prato, K. Kostarelos, A. Bianco, *Acc. Chem. Res.,* 2008, 41, 60-68; b) J. Cheon, J.-H. Lee, *Acc. Chem. Res.,* 2008, 41, 1630-1640; c) B. G. Trewyn, I. I. Slowing, S. Giri, H.-T. Chen, V. S.-Y. Lin, *Acc. Chem. Res.,* 2007, 40, 846-853; d) I. I. Slowing, J. L. Vivero-Escoto, C.-W. Wu, V. S.-Y. Lin, *Adv. Drug Deliv. Rev.,* 2008, 60, 1278-1288; e) C. J. Murphy, A. M. Gole, J. W. Stone, P. N. Sisco, A. M. Alkilany, E. C. Goldsmith, S. C. Baxter, *Acc. Chem. Res.,* 2008, 41, 1721-1730

[79] M.-C. Daniel, D. Astruc, *Chem. Rev* 2004, 104, 293-346.

[89] a) K. K. Sandhu, C. M. McIntosh, J. M. Simard, S. W. Smith, V. M. Rotello, *Bioconjugate Chem.* 2002, 13, 3-6; b) ACS nano 2008, 2213; c) M. Thomas, A. M. Klibanov, *Proc. Natl. Acad. Sci. U.S.A.* 2003, 100, 9138-9143; d) C. Agbasi-Porter, J. Ryman-Rasmussen, S. Franzen, D. Feldheim, *Bioconjugate Chem.* 2006, 17, 1178-1183; e) C.-Y. Tsai, A.-L. Shiau, P.-C. Cheng, D.-B. Shieh, D.-H. Chen, C.-H. Chou, C.-S. Yeh, C.-L. Wu, *Nano lett.* 2004, 4, 1209-1212; f) N. L. Rosi, D. A. Giljohann, C. S. Thaxton, A. K. R. Lytton-Jean, M. S. Han, C. A. Mirkin, *Science* 2006, 312, 1027-1030.

[99] J.-R. Bertrand, M. Pottier, A. Vekris, P. Opolon, A. Maksimenko, C. Malvy, *Biochem. Biophys. Res. Commun.* 2002, 296, 1000-1004.

[109] S. J. Hurst, A. K. R. Lytton-Jean, C. A. Mirkin, *Anal. Chem.* 2006, 78, 8313-8318.

[119] C. Skoda, B. M. Erovic, V. Wachek, L. Vormittag, F Wrba, H. Martinek, G. Heiduschka, P. Kloimstein, E. Selzer, D. Thurnher, *Oncol. Rep.* 2008, 19, 1499-1503.

[129] R. Agami, R. Bernards, *Cell,* 2000, 102, 55-66.

[139] L.-C. Dai, X. Wang, X. Yao, L.-S. Min, F.-C. Qian, J.-F. He, *Acta Pharmacologica Sinica* 2006, 27, 1453-1458.

[149] S. Bi, F. Lanza, J. M. Goldman, *Cancer Research* 1994, 54, 582-586.

[159] a) Z. Wang, A. G. Kanaras, A. D. Bates, R. Cosstick, M. Brust, *J. Mater. Chem.* 2004, 14, 578; b) D. S. Seferos, A. E. Prigodich, D. A. Giljohann, P. C. Patel, C. A. Mirkin, *Nano Lett* 2009, 9, 308-311.

[169] T. R. Brummelkamp, R. Bernards, R. Agami, A system for stable expression of short interfering RNAs in mammalian cells, Science 296 (2002) 550-553.

[179] M. Taniai, A. Grambihler, H. Higuchi, N. Werneburg, S. F. Bronk, D. J. Farrugia, S. H. Kaufmann, G. J. Gores, Mcl-1 mediates tumor necrosis factor-related apoptosis-inducing ligand resistance in human cholangiocarcinoma cells, Cancer Res. 64 (2004) 3517-3524.

[189] B. Polisky, ColE1 replication control circuitry: sense from antisense, *Cell* 55 (1988) 929-932.

What is claimed is:

1. A method for delivering a cargo into human cells, comprising contacting a gene delivery system with the human cells, thereby delivering the cargo into the human cells, wherein the gene delivery system comprises: (a) a nanomaterial which is a gold nanoparticle with the size range of 1-100 nm, wherein the nanomaterial is penetrated into the human cell by said method; (b) an oligonucleotide as a universal binding partner covalently linked to the surface of the nanomaterial by means of a thiol group bound to the end of the universal binding partner, wherein the universal binding partner is the nucleotide sequence of SEQ ID NO:2; and (c) a cargo comprising (i) a complementary oligonucleotide containing a nucleotide sequence complementary to the universal binding partner as a binding counter-partner, and (ii) an inhibitory molecule having a nucleotide sequence complementary to a target gene of interest to be inhibited or an inducible molecule that is an expression construct containing a promoter, and a coding sequence of a target gene of interest to be expressed operatively linked to the promoter, and wherein the inhibitory molecule or the inducible molecule is linked to the binding counter-partner.

2. The method according to claim 1, wherein the nanomaterial is a gold nanoparticle with the size range of 8-100 nm.

3. The method according to claim 1, wherein the complementary oligonucleotide as the binding counter-partner is 3-100 nucleotides in length.

4. The method according to claim 1, wherein the inhibitory molecule having the nucleotide sequence complementary to the target gene of interest to be inhibited in step (c) comprises an antisense oligonucleotide, an aptamer, an siRNA, an shRNA, an miRNA, a ribozyme, a DNAzyme, or a PNA (peptide nucleic acid).

* * * * *